US009290617B2

(12) United States Patent
Shoichet et al.

(10) Patent No.: US 9,290,617 B2
(45) Date of Patent: Mar. 22, 2016

(54) METHOD OF BIOMOLECULE IMMOBILIZATION ON POLYMERS USING CLICK-TYPE CHEMISTRY

(75) Inventors: Molly S. Shoichet, Toronto (CA); Yumin Yuan, Jiaxing (CN); Meng Shi, Toronto (CA); Jordan Wosnick, Toronto (CA)

(73) Assignee: Molly S. Shoichet, Toronto, ON (CA)

( * ) Notice: Subject to any disclaimer, the term of this patent is extended or adjusted under 35 U.S.C. 154(b) by 1067 days.

(21) Appl. No.: 11/988,207

(22) PCT Filed: Jul. 6, 2006

(86) PCT No.: PCT/CA2006/001100
§ 371 (c)(1),
(2), (4) Date: Apr. 11, 2008

(87) PCT Pub. No.: WO2007/003054
PCT Pub. Date: Jan. 11, 2007

(65) Prior Publication Data
US 2009/0297609 A1    Dec. 3, 2009

Related U.S. Application Data

(60) Provisional application No. 60/696,506, filed on Jul. 6, 2005.

(51) Int. Cl.
*A61K 47/00* (2006.01)
*C08G 64/00* (2006.01)
(Continued)

(52) U.S. Cl.
CPC ........ *C08G 63/912* (2013.01); *A61K 47/48907* (2013.01); *C08G 63/64* (2013.01); *C08G 64/0241* (2013.01); *C08G 64/42* (2013.01)

(58) Field of Classification Search
CPC ....... A61K 9/14; A61K 39/395; A61K 35/12; A61K 35/76; A61K 3/7088; C08F 18/24; C08F 24/00; C08F 116/02; C07C 43/00
See application file for complete search history.

(56) References Cited

U.S. PATENT DOCUMENTS 6,083,524 A   7/2000   Sawhney et al.
6,737,236 B1 * 5/2004  Pieken et al. ............... 435/6
(Continued)

FOREIGN PATENT DOCUMENTS

CA       2286320      10/1998
WO    WO9928354 A2    6/1999
WO    WO2007011696 A2 1/2007

OTHER PUBLICATIONS

Kolb et al., (Drug Discovery Today. Dec. 24, 2003:8;1128-1137).*
(Continued)

*Primary Examiner* — Cherie M Stanfield
(74) *Attorney, Agent, or Firm* — Fish & Richardson P.C.

(57) ABSTRACT

The present invention provides a method for the covalent immobilization of biomolecules on polymers for delivery of the biomolecules, which has the advantage of being simple, highly efficient, environmentally friendly and free of side products relative to traditional immobilization techniques. The invention provides a modified micro/nanoparticle system, which uses a functionalized polymer formed into micro or nanoparticles to bind a molecule to the particles using uses facile chemistry, the Diels-Alder cycloaddition between a diene and a dienophile with the polymer being functionalized with one of them and the molecule with the other, or the Huisgen 1,3-dipolar cycloaddition between a terminal alkyne and an azide to bind the molecule to the particle. The molecules and/or other therapeutic agents may be encapsulated within the polymer particles for intravenous therapeutic delivery. The invention also provides a novel synthetic biodegradable polymer, a furan/alkyne-functionalized poly(trimethylene carbonate) (PTMC)-based polymer, whose composition can be designed to meet the defined physical and chemical property requirements. In one example, the particle system self-aggregates from functionalized PTMC-based copolymers containing poly(ethylene glycol) (PEG) segments. The composition of the copolymers can be designed to meet various particle system requirements, including size, thermodynamic stability, surface PEG density, drug encapsulation capacity and biomolecule immobilization capacity.

37 Claims, 16 Drawing Sheets

(51) Int. Cl.
*C08G 63/91* (2006.01)
*C08G 63/64* (2006.01)
*C08G 64/02* (2006.01)
*C08G 64/42* (2006.01)
*A61K 47/48* (2006.01)

(56) References Cited

U.S. PATENT DOCUMENTS

2005/0032081 A1* 2/2005 Ju et al. .............................. 435/6
2006/0058266 A1* 3/2006 Manoharan et al. ............ 514/81

OTHER PUBLICATIONS

Edlund et al., (Biomaterials. May 2000;21(9):945-55, Abstract Only).*
Calderone et al., (Eur J. Med Chem. Jun. 2005;40(6):521-8. Epub Mar. 3, 2005, Abstract Only).*
D. Hayworth, Polyethylene Glycol (PEG) and Pegylation of Proteins. www.piercenet.com/method/polyethylene-glycol-peg-pegylation) (last accessed Jun. 12, 2014).*
IUPAC. Compendium of Chemical Terminology, 2nd ed. (the "Gold Book"). Compiled by A.D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. Last accessed Jun. 12, 2014. Definitions.*
Hayworth ("Polyethylene Glycol (PEG) and Pegylation of Proteins." www.piercenet.com/method/polyethylene-glycol-peg-pegylation) (last accessed Jun. 12, 2014).*
Anderson et al., (Polymer. Dec. 2004. 45:8809-8823).*
S.A. Hagan, et al., (Langmuir, vol. 12, No. 9, 1996, pp. 2153-2161).*
Dong et al., (Biomaterials. 2004. 25:2843-2849).*
Fisera et al., (Chem Papers. 1995. 49(4):186-191).*
Gandini (Polimeros Ciencia e Technologia. 200515(2):95-101).*
Shin et al., (J Controlled Release. 1998;51:1-11).*
Zhang et al., (J Controlled Release. 2006;111:263-270).*
Zhang et al., (Biomaterials. 2005;26:2089-2094).*
Kolb, H.C. et al. *Click Chemistry: Diverse Chemical Function from a Few Good Reactions.* Angewandte Chemie Int. Ed., 2001, vol. 40.
Kolb, H.C. et al. *The growing impact of click chemistry on drug discovery.* Drug Discovery Today, 2003, vol. 8, No. 24.
Lietz, M. et al. *Physical and Biological Performance of a Novel Block Copolymer Nerve Guide.* Biotechnology and Bioengineering, Sep. 26, 2005 on-line, vol. 93, No. 1.
Dinarvand, R. et al. *In vitro release of clomipramine HCL and buprenorphine HCL from poly anhydride (PAA) and poly trimethylene carbonate (PTMC) blends.* Journal of Biomedical Materials Research, Part A, Jul. 25, 2005 on-line, vol. 75A, No. 1.
Grether et al., 'An Enzyme-Labile Safety Catch Linker for Synthesis on a Soluble Polymeric Support,' Chemistry—A European Journal, vol. 7, No. 5, Jan. 1, 2001, pp. 959-971.
Groth et al., 'Peg Based Resins for Protease Drug Discovery Synthesis, Screening and Analysis of Combinatorial On-Bead Libraries,' Combinatorial Chemistry & High Throuhput Screening, 6, pp. 589-610, 2003.
Joralemon et al., "Shell Click-Crosslinked (SCC) Nanoparticles: A New Methodology for Synthesis and Orthogonal Functinalization," Journal of the American Chemical Society, vol. 127, pp. 16892-16899, Dec. 1, 2005.
Pan et al., 'Folic acid-conjugated Nanostructured Materials Designed for Cancer Cell Targeting,' Chemical Communications, No. 19, Oct. 7, 2003.
Roice et al., 'High Capacity Poly(ethylene Glycol) Based Amino Polymers for Peptide and Organic Synthesis,' Qsar and Combinatorial Science, vol. 23, No. 8, pp. 662-673, Jan. 1, 2004.
Storey et al., 'Methacrylate-endcapped poly (d. 1-lactide-co-trimethylene carbonate) oligomers. Network formation by thermal free-radical curing,' Polymer, vol. 38, No. 26, pp. 6295-6301, 1997.
Thomas et al., 'Covalent Adhesion; Organic Reactivity at a Solid-solid Interface through an Inter-bead Diels-Alder Reaction', Chemical Communications, No. 16, pp. 1507-1508, Aug. 21, 1999.
Supplementary European Search Report dated Mar. 25, 2013, EP Application No. 06752870.3, 15 pgs.

* cited by examiner

Florescence-labeled anti-HER2 immuno-nanoparticles bound with SKBR3.

Negative control I: SKBR3 alone

Control II: Fluorescence-labeled nanoparticles did not bind with SKBR3.

Control III: Blank nanoparticles did not bind with SKBR3.

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Gly Asp Pro Gly Tyr Ile Gly Ser Arg
1               5
```

METHOD OF BIOMOLECULE IMMOBILIZATION ON POLYMERS USING CLICK-TYPE CHEMISTRY

CROSS REFERENCE TO RELATED U.S. PATENT APPLICATION

This patent application is a National Phase application for patent claiming the benefit of PCT/2006/001100; which further claims the priority benefit from U.S. provisional patent application Ser. No. 60/696,506 filed on Jul. 6, 2005 entitled METHOD OF BIOMOLECULE IMMOBILIZATION ON POLYMERS USING CLICK-TYPE CHEMISTRY, filed in English, which is incorporated herein in its entirety by reference.

SEQUENCE LISTING

This application incorporates-by-reference the material included on a written copy of a sequence listing included with the application, as well as on a computer readable copy of the sequence listing submitted on one compact disc. The disc was created on Jul. 30, 2009, and includes one 2 KB file entitled, "402003.sequence.txt." The copy of the computer readable form of the sequence listing is identical to the written copy of the sequence listing, and thus, the computer readable copy includes no new matter.

FIELD OF THE INVENTION

The present invention relates to the field of biotechnology. Specifically, this invention provides a simple chemistry to immobilize biological molecules onto synthetic biodegradable polymers. The system, comprising a polymeric carrier and an immobilized biomolecule, introduces a specific cell-material interaction with many biomedical and non-biomedical applications such as in drug delivery, biosensors, medical implant materials, bioseparations, bioreactors, and biocatalysis.

BACKGROUND OF THE INVENTION

The design of polymer-biomolecule hybrid biomaterials with precisely defined properties has been proven to be critical in many biological applications. Immobilization of monoclonal antibodies/peptides on polymeric particles allows for targeted drug delivery (B. A. Khaw, Encyclopedia of pharmaceutical Technology 1998:2733; F. Marcucci et al., Drug Discovery Today 2004, 9:219). Immobilization of peptides/proteins on polymeric surfaces is of great interest for the development of biosensors and medical materials (M. Tirrell et al., Surface Science 2000, 500:61), while the immobilization of enzymes on polymeric fibers enables the preparation of biocatalysts (P. Gemeiner, In Enzyme Engineering: Immobilized Biosystems 1992:167).

Since biomolecules are much more chemically sensitive than typical small organic molecules, the choice of methods for covalent bond formation between biomolecules and polymers is limited to those occurring under specific and sufficiently mild conditions, which usually include aqueous solutions with pH values between 6 and 8, temperatures less than 37° C., and the absence of any reagents which may induce denaturation of biomolecules (L. Nobs et al., Journal of Pharmaceutical Sciences 2004, 93:1980).

The immobilization of biomolecules by binding them covalently to pre-formed polymers is based on the reaction between the functional groups on biomolecules and polymers. There are various natural or synthetic polymers with functional groups that have been reported for this purpose (M. I. Shtilman, Immobilization on Polymers 1993:341). In most cases, carboxylic acid, amine, or thiol groups on biomolecules take part in the reactions with the involvement of cross-linkers (G. T. Hermanson, Bioconjugate Techniques 1996:137). Those traditional immobilization methods can be limited by the operational complexity of the reaction procedure, the involvement of organic solvent or offensive reagents, instability of the functional groups, possible side-reactions and low immobilization efficiency (V. P. Torchilin, Biochimica et Biophysica Acta 2001, 1511:397; T. M. Allen, Biochimica et Biophysica Acta 1995, 1237:99).

There is therefore a need for simple, clean, and highly efficient immobilization chemistries which are applicable to a broad class of biomolecules. The concept of "click chemistry" was first introduced in 2001 (H. C. Kolb et al., Angewandte Chemie International Edition 2001, 40:2005). Sharpless and co-workers have used the term to describe chemical reactions that occur rapidly and selectively, without prior activation, and with high atom economy. Prototypical "click" reactions include cycloadditions of unsaturated species (especially the [2+3] Huisgen addition of azides to alkynes); nucleophilic substitution chemistry; carbonyl chemistry of the "non-aldol" type; and additions of carbon-carbon multiple bonds, including Diels-Alder chemistry. These reactions are diverse in scope yet orthogonal in reactivity, give very high yields, produce only inoffensive byproducts or no byproducts, occur under simple reaction conditions, and use benign solvents (including water). The strategy has been successfully utilized for rapid synthesis of small molecule libraries and enzyme inhibitors (H. C. Kolb et al., Drug Discovery Today 2003, 8:1128).

SUMMARY OF THE INVENTION

The present invention provides a novel method for the covalent immobilization of molecules on polymer nanoparticles or microparticles for targeted delivery of the molecules, which has the advantage of being simple, highly efficient, environmentally friendly and free of side products relative to traditional immobilization techniques.

Thus, in one aspect of the invention there is provided a composition for therapeutic delivery of a molecule, comprising: composition for therapeutic delivery of a molecule, comprising:

a polymer nanoparticle or microparticle comprised of a polymer functionalized to include a first unsaturated functional group; and a molecule functionalized to include a second unsaturated functional group, said first and second functional groups being complementary to each other and being selected such that said first and second unsaturated functional group react with each other by one of Diels-Alder cycloaddition and Huisgen 1,3-dipolar cycloaddition to covalently bind the molecule to said polymer nanoparticle or microparticle to form a delivery vehicle for therapeutic delivery of said molecule.

The method is based on the principle of functionalizing a polymer (in the form of a microparticle or nanoparticle) preferably with a diene, and functionalizing the molecule to be immobilized thereon with a complementary dienophile, or vice versa (so that if the polymer is functionalized with the complementary dienophile, the molecule to be immobilized thereon is functionalized with the diene), and using cycloaddition chemistry, specifically the Diels-Alder cycloaddition between the diene and the dienophile, to chemically bind the molecule to the polymer. Alternatively, the polymer may be functionalized with a terminal alkyne and the molecule to be bound thereto is functionalized with a complementary azide, or vise versa (so that the polymer is functionalized with the azide and the molecule to be immobilized thereon is functionalized with the alkyne) and the molecule is bound to the polymer using the Huisgen 1,3-dipolar cycloaddition between a terminal alkyne and an azide (preferably a Cu(I)-catalyzed cycloaddition).

The molecules chemically bound to the nano/microparticles may be biomolecules having a therapeutic function. In this aspect of the invention the polymers may be of natural origin including but not limited to proteins, polypeptides, polysialic acids, hyaluronic acid and derivatives thereof, polysaccharides, chitosan and derivatives thereof, alginate and derivatives thereof, dextran and derivatives thereof, and aliphatic poly(esters), polycarbonates and derivatives thereof, poly(hydroxyalkanoates) and derivatives thereof. The polymers may be produced by chemical synthesis including polymers produced by ring-opening polymerization, polycondensation, free radical polymerization, or ionic polymerization. The polymers may be produced by biological synthesis and may include polymers synthesized by fermentation.

The nanoparticles/microparticles can be used to encapsulate one or more therapeutic agents in the interior of the polymer particles for targeted therapeutic delivery. The therapeutic agents may be the same molecule bound to the micro/nanoparticle by Diels-Alder cycloaddition chemistry or Huisgen 1,3-dipolar cycloaddition, or it may simply be encapsulated inside the particle without being chemically bound. In addition, the therapeutic agents encapsulated in the interior may also include nucleic acids (DNA, cDNA, RNA, and PNA), proteins (including but not limited to antibodies, antibody fragments, enzymes, ligands, receptors, viral vectors, and viruses), small molecules (such as polypeptides, peptides, amino acids, metabolites and drugs), and other biomolecules (such as vitamins, antibiotics, hormones, or even entire cells) for targeted delivery of the therapeutic agent(s). The therapeutic molecule may be immobilized to the micro/nanoparticle by one of the cycloaddition reactions or it may be encapsulated within. The therapeutic molecule may provide a therapeutic capacity and a targeting capacity.

The present invention also provides a method of delivery of a molecule, comprising:

a) providing nanoparticles or microparticles of a polymer functionalized to include a first unsaturated functional group;

b) providing a molecule functionalized with a second unsaturated functional group, said first and second functional groups being complementary to each other and being selected such that said first and second unsaturated functional groups react with each other by one of Diels-Alder cycloaddition and Huisgen 1,3-dipolar cycloaddition;

c) mixing said nanoparticles or microparticles with said molecule under conditions suitable to react said first unsaturated functional group on said polymer nanoparticle or microparticle with said second unsaturated functional group on said molecule by one of Diels-Alder cycloaddition and Huisgen 1,3-dipolar cycloaddition to covalently bind the molecule to said polymer nanoparticle or microparticle to form a delivery vehicle for said molecule; and d) introducing said nanoparticles or microparticles having said molecule bound thereto into a biological system.

The present invention also provides polymer, comprising:

a poly(trimethylene carbonate) (PTMC)-based polymer functionalized to include a first unsaturated functional group which reacts with a second unsaturated functional group, said first and second functional groups being complementary to each other and being selected such that said first and second unsaturated functional groups react with each other by one of Diels-Alder cycloaddition and Huisgen 1,3-dipolar cycloaddition for covalently binding the second unsaturated functional group to the first unsaturated functional group on said polymer.

Preferably the poly(trimethylene carbonate) (PTMC)-based polymer is functionalized to bear a diene or dienophile for Diels-Alder cycloaddition (or an alkyne or azide for Huisgen 1,3-dipolar cycloaddition) as discussed above, whose composition can be designed to meet the defined physical and chemical property requirements.

This novel functionalized PTMC polymer may be formed into a micro/nanoparticle system, which can have desired molecules (suitably functionalized) chemically bound to the particle by the Diels-Alder cycloaddition and/or Huisgen 1,3-dipolar cycloaddition depending on the functional groups added to the polymer. The nanoparticles/microparticles can be used to encapsulate one or more therapeutic agents for targeted therapeutic delivery. The particle system self-aggregates from functionalized poly(trimethylene carbonate) (PTMC)-based copolymers containing poly(ethylene glycol) (PEG) segments. The composition of the copolymers can be designed to meet various particle system requirements, including size, thermodynamic stability, surface PEG density, drug encapsulation capacity and biomolecule immobilization capacity.

The therapeutic agent may be the same molecule bound to the micro/nanoparticle by Diels-Alder cycloaddition chemistry or Huisgen 1,3-dipolar cycloaddition, or it may simply be encapsulated inside the particle without being chemically bound. The therapeutic agent may also serve as a targeting ligand to specific cells or tissues. The therapeutic agents may include nucleic acids (DNA, cDNA, RNA, and PNA), proteins (including but not limited to antibodies, antibody fragments, enzymes, ligands, receptors, viral vectors, and viruses), small molecules (such as polypeptides, peptides, amino acids, metabolites and drugs), and other biomolecules (such as vitamins, antibiotics, hormones, or even entire cells) for targeted delivery of the therapeutic agent(s).

A further understanding of the functional and advantageous aspects of the invention can be realized by reference to the following detailed description and drawings.

BRIEF DESCRIPTION OF THE DRAWINGS

The method of biomolecule immobilization on polymers using click-type chemistry according to the present invention will now be described, by way of example only, reference being made to the accompanying drawings, in which.

Figure 1:
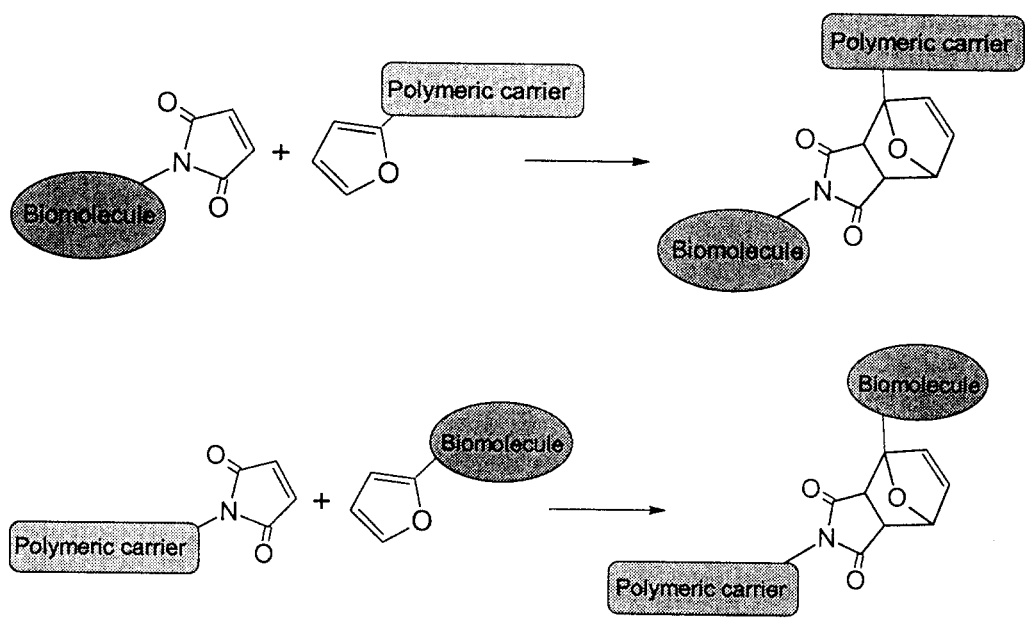
FIG. 1 is a diagrammatic illustration of biomolecule immobilization on a polymeric carrier by Diels-Alder cycloaddition.

Table 1 summarizes the characterization of poly(TMCC-co-LA)-g-PEG-furan copolymers;

Table 2 summarizes the characterization of furan-substituted poly(allylTMC-co-LA) copolymers;

Table 3 summarizes the characterization of poly(furfurylTMC-co-LA) copolymers;

Table 4 summarizes the effective diameters of the self-aggregated nanoparticles;

Table 5 summarizes the characterization of hydrophobic drug encapsulation of copolymer nanoparticles;

Table 6 summarizes the characterization of protein drug encapsulation of copolymer nanoparticles.

DETAILED DESCRIPTION OF THE INVENTION

As used herein, the term "microparticle" includes a microsphere and means a particle between about 1 micron and about 1 millimetre in size, and the term "nanoparticle" includes a nanosphere and means a particle between about 1 nanometre and about 1 micron in size.

The present invention provides a novel method for the covalent immobilization of molecules on polymer nanoparticles or microparticles for targeted delivery of molecules. A polymer in the form of a microparticle or nanoparticle is functionalized with a diene, and the molecules to be bound to the particle are functionalized with a complementary dienophile, or vice versa (so that if the polymer is functionalized with the complementary dienophile, the molecules are functionalized with the diene), and cycloaddition chemistry, specifically the Diels-Alder cycloaddition between the diene and the dienophile, is used to chemically bind the molecule to the polymer particle. Alternatively, the polymer may be functionalized with a terminal alkyne and the molecules to be bound thereto are functionalized with a complementary azide, or vise versa (so that the polymer is functionalized with the azide and the molecules to be immobilized thereon are functionalized with the alkyne) and the molecules are bound to the polymer using the Huisgen 1,3-dipolar cycloaddition between a terminal alkyne and an azide (preferably a Cu(I)-catalyzed reaction).

The polymer particles could also be functionalized with both dienes and dienophiles and the molecules could also include dienes and dienophiles and if one type of molecule is being immobilized some of them may be functionalized with the dienes and the remainder with the dienophiles. Alternatively, if more than one type of molecule is being bound, one type may be functionalized with the dienes and the other with the dienophiles. The same applies for the polymers functionalized with alkynes and azides, such that the polymer particle may contain both groups, and if one type of molecule is being immobilized some of them may be functionalized with the alkynes and the remainder with the azides. Alternatively, if more than one type of molecule is being bound, one type may be functionalized with the azide and the other with the alkyne.

When the polymer/molecule are functionalized using dienes/dienophiles, and the Diels-Alder cycloaddition reaction is used to covalently bind the two, the diene may include for example furan and derivatives thereof, cyclopentadiene and derivatives thereof, butadiene and derivatives thereof, or cyclohexadiene and derivatives thereof. The dienophile may include maleimide and derivatives thereof, acrylonitrile and derivatives thereof, acrylamide and derivatives thereof, methyl vinyl ketone and derivatives thereof, esters of maleic acid and derivatives thereof, esters of fumaric acid and derivatives thereof, esters of acrylic acid and derivatives thereof, maleic anhydride and derivatives thereof, esters and amides of but-2-ynedioic acid and derivatives thereof, quinone and derivatives thereof, and substituted acetylenes and derivatives thereof.

When the polymer/molecule are functionalized using alkynes/azides and the Huisgen 1,3-dipolar cycloaddition reaction is used to covalently bind the two, the alkyne may be terminal alkynes substituted with alkyl groups and derivatives thereof, ester groups and derivatives thereof, amide groups and derivatives thereof, alkyl and polyoxoalkyl groups and derivatives thereof, aryl and derivatives thereof, phenyl groups and derivatives thereof, and benzyl groups and derivatives thereof. The azide may be alkyl and polyoxoalkyl azides and derivatives thereof, aryl azides and derivatives thereof, benzyl azides and derivatives thereof.

The polymers may be block copolymers, copolymers, terpolymers, graft copolymers, graft terpolymers or amphiphilic copolymers. The polymers may be of natural origin, including but not limited to proteins, polypeptides, polysialic acids, hyaluronic acid and derivatives thereof, polysaccharides, chitosan and derivatives thereof, alginate and derivatives thereof, dextran and derivatives thereof, and aliphatic poly(esters), polycarbonates and derivatives thereof, poly(hydroxyalkanoates) and derivatives thereof. The polymers may be produced by chemical synthesis including polymers produced by ring-opening polymerization, polycondensation, free radical polymerization, or ionic polymerization. The polymers may be produced by biological synthesis and may include polymers synthesized by fermentation. The molecules chemically bound to the nano/microparticles may be biomolecules having a therapeutic function.

Thus, in this invention, examples of types of the polymers include, but are not limited to, functionalized biodegradable polymers with at least one unsaturated functional group which performs at least one kind of Diels-Alder cycloaddition reaction or 1,3-dipolar Huisgen cycloaddition reaction, such as furan- (or maleimide-) functionalized PTMC homopolymers, furan-functionalized PTMC-based copolymers from PTMC and other biodegradable polymers such as poly(D,L-lactide) (PLA), poly(glycolic acid) (PGA) and poly(lactic acid-co-glycolic acid) (PLGA), and functionalized PTMC-based copolymers containing PEG segments such as poly(TMCC-co-LA)-g-PEG-furan, poly(TMCC-co-LA)-g-PEG-alkyne, poly(TMCC-co-LA)-g-PEG-furan (and alkyne) and poly(TMCC-co-LA)-g-PEG-azide copolymers, PTMC-PEG diblock copolymers, and PEG-PTMC-PEG triblock copolymers. As discussed above, other biodegradable polymers that can be formulated as microparticles and/or nanoparticles (or microspheres and/or nanospheres) and are modified with a functional group capable of Diels-Alder or Huisgen cycloaddition also fall within the scope of the present invention.

As mentioned above, the present invention also provides a new synthetic biodegradable polymer as a carrier for biomolecules, and a new biomolecule immobilization methodology based on at least one of the Diels-Alder cycloaddition reaction and the Huisgen 1,3-dipolar cycloaddition reaction. Basically, the polymeric carriers are prepared from pre-synthesized PTMC-based biodegradable polymers, with outer/inner surface bearing at least one unsaturated functional group which performs at least one of the Diels-Alder cycloaddition reaction and the Huisgen 1,3-dipolar cycloaddition reaction. Biomolecules are specifically modified to introduce the corresponding functional groups. The reaction between the two functional groups fulfills the criteria for "click"-type chemistry, as described by Sharpless: to be simple (a one-step reaction without by-products), clean (no initiator or coupling reagents are involved), environmentally friendly (reaction proceeds in aqueous solution), highly efficient, and relatively rapid under physiological conditions, with stable products.

Figure 2:
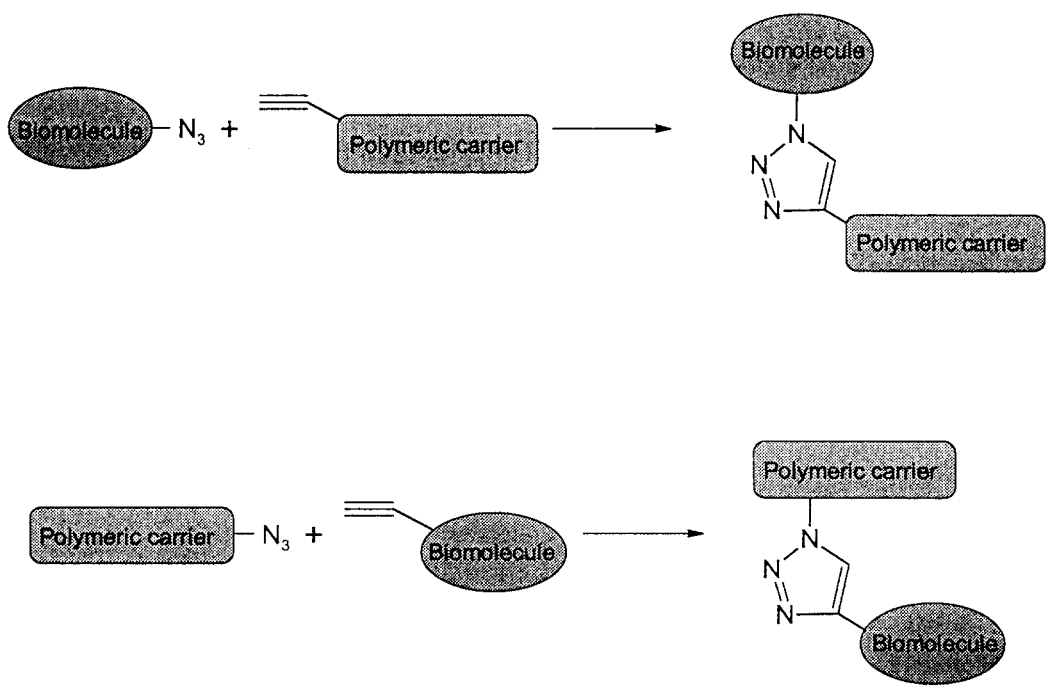
FIG. 2 shows a diagrammatic illustration of biomolecule immobilization on a polymeric carrier by Cu(I)-catalyzed Huisgen 1,3-dipolar cycloaddition.

The superior reactions employed in this invention have the general descriptions given below. Referring to FIGS. 1 and 2, both Diels-Alder cycloadditions and Cu(I)-catalyzed Huisgen 1,3-dipolar cycloadditions involve two unsaturated reactants and provide fast access to five- or six-membered rings.

In Example 1, furan-functionalized poly(TMCC-co-LA)-g-PEG 1 (FIG. 4), furan-substituted poly(allylTMC-co-LA) 2 (FIG. 5) and poly(furfurylTMC-co-LA) 3 (FIG. 6) were synthesized by different routes for Diels-Alder reaction. The furan group was chosen as the diene function on the polymer surface because of its wide availability in small molecules, which allows for the functionalization of the polymers simply and easily before or after polymerization. In addition, due to its high stability under polymerization conditions, a broad class of PTMC-based homopolymers and copolymers can be synthesized starting from the new furan-containing monomers.

Figure 3:
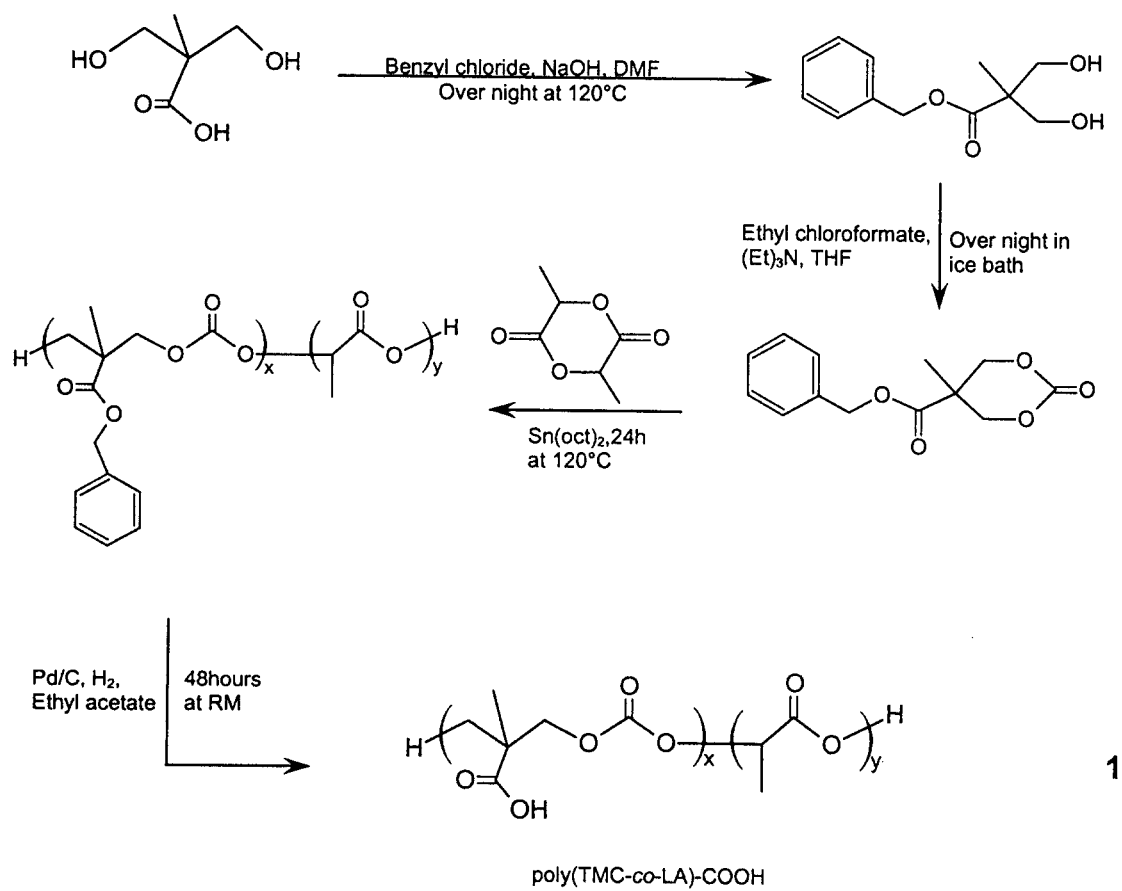
FIG. 3 shows an exemplary synthesis of carboxylic acid-substituted poly(trimethylene carbonate-co-lactide) [poly(TMCC-co-LA)] copolymer.
Figure 4:
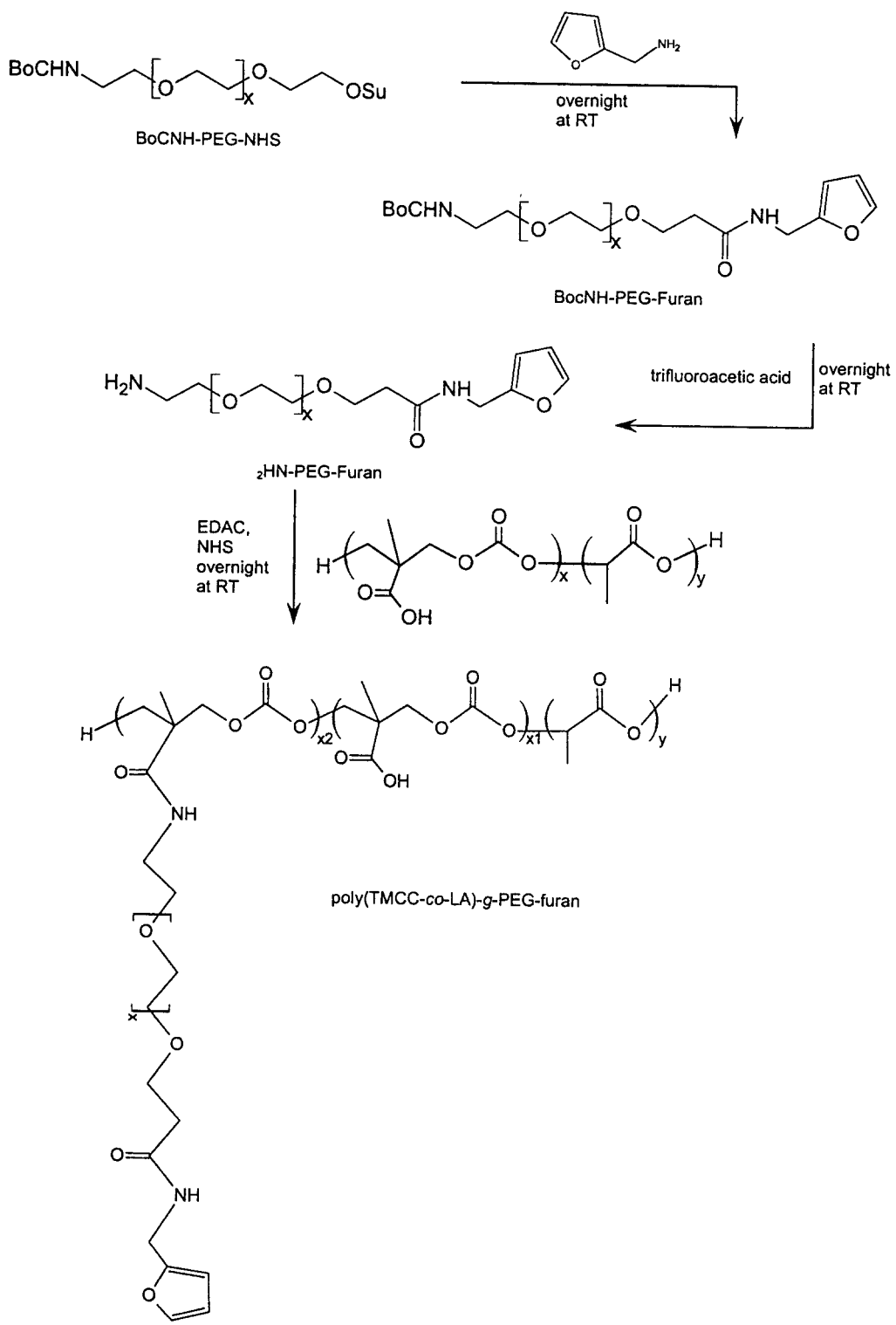
FIG. 4 shows an exemplary synthesis of poly(trimethylene carbonate-co-lactide) grafted with PEG-furan [poly(TMCC-co-LA)-g-PEG-furan] copolymer.
Figure 7:
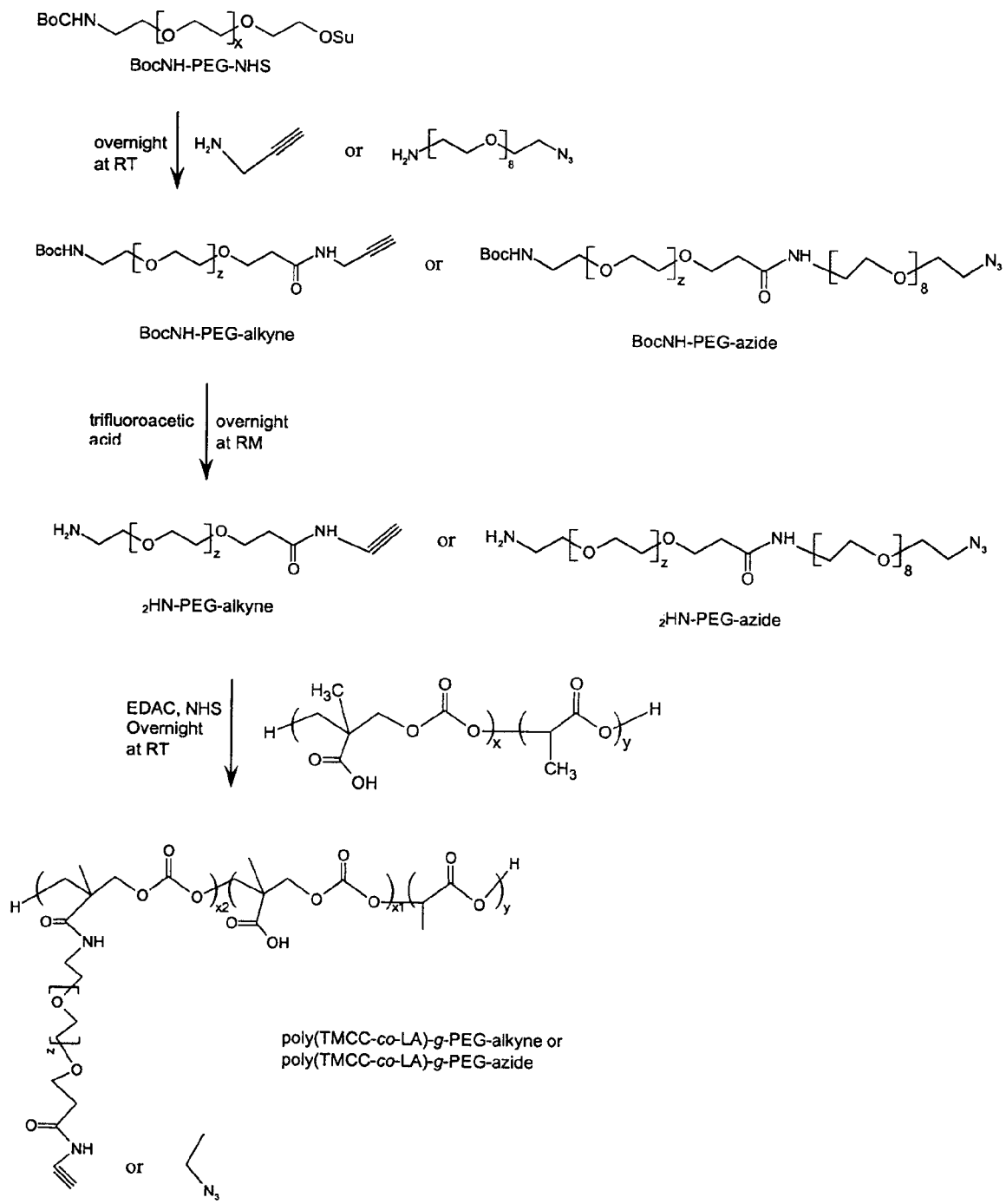
FIG. 7 shows an exemplary synthesis of poly(TMCC-co-LA)-g-PEG-alkyne (or azide) copolymer.
Figure 8:
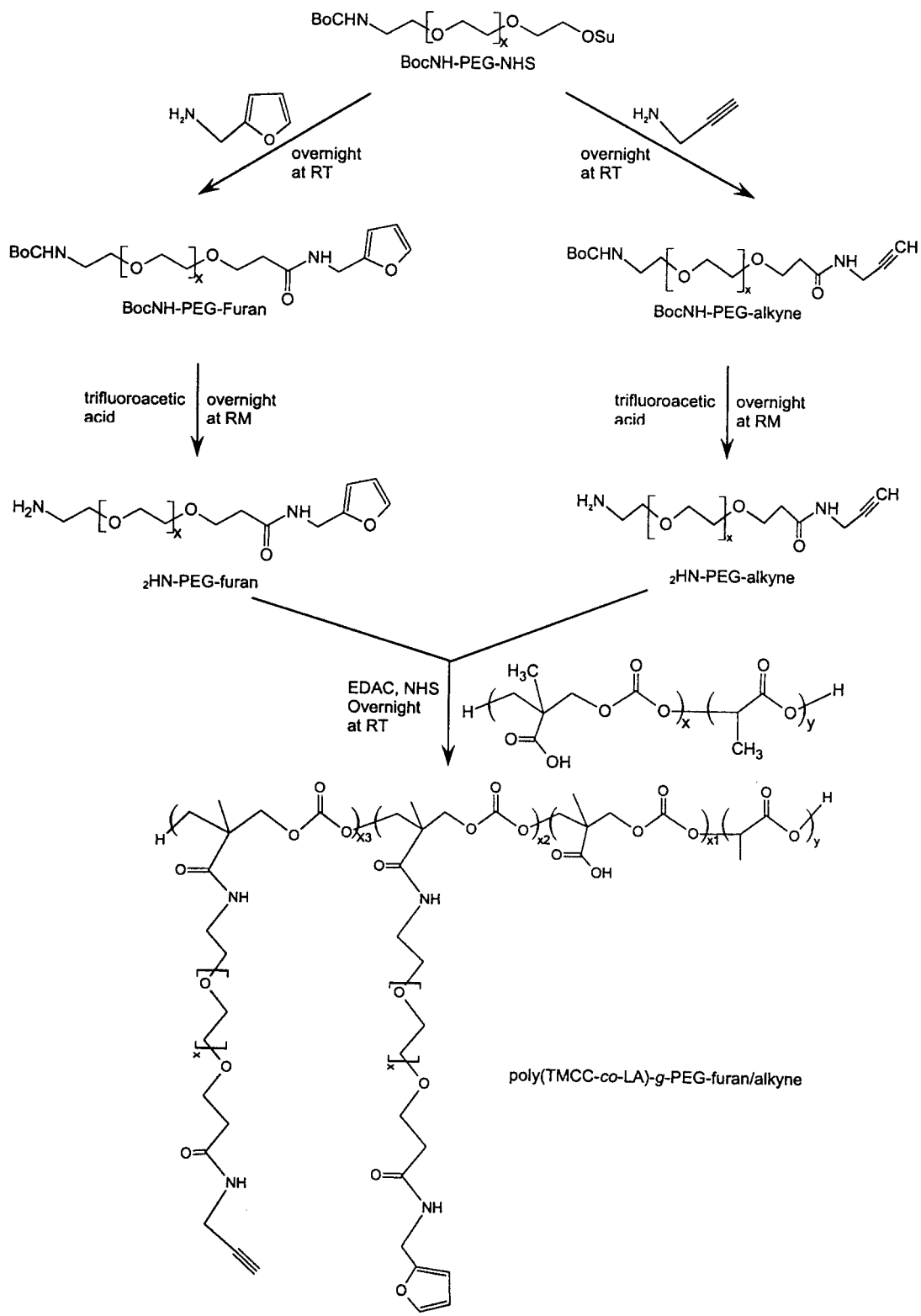
FIG. 8 shows an exemplary synthesis of poly(TMCC-co-LA)-g-PEG-furan (and alkyne) copolymer

To prepare the furan-functionalized PTMC-based copolymer containing poly(ethylene glycol) (PEG) segments, furan-modified PEG chains were grafted on carboxylic acid-substituted poly(trimethylene carbonate-co-D,L-lactide) (poly (TMCC-co-LA)) to yield poly(TMCC-co-LA)-g-PEG-furan (FIG. 3 and FIG. 4). In a similar synthesis route, the poly (TMCC-co-LA)-g-PEG-alkyne (or azide) and poly(TMCC-co-LA-g-PEG-furan (and alkyne) were prepared to bear alkyne (or azide) on the polymer for Cu(I)-catalyzed Huisgen 1,3-dipolar cycloadditions (FIG. 7 and FIG. 8). In Example 1, the novel furan-containing poly(TMC-co-LA) copolymers 2 and 3 were synthesized by two different routes. In synthesis route 1 (FIG. 5), the novel allyl-containing poly(allylTMC-co-LA) was polymerized first and then reacted with furfuryl mercaptan to introduce furan groups into the copolymers (furan-substituted poly(allylTMC-co-LA)). In synthesis route 2 (FIG. 6), the novel furan-containing monomer 5-furfurylamide-5-methyl-1,3-dioxane-2-one was synthesized and then copolymerized with D,L-lactide monomers to yield poly(furfurylTMC-co-LA) copolymers with freely adjusted furan concentrations and physical properties for film preparation.

The polymer design in this invention provides for an unexpected degree of control over the physical and chemical properties of the polymers, which can fulfill specific requirements for the preparation and use of polymeric carriers. Examples of the polymeric carriers include, but are not limited to, single polymer chains, microparticles, nanoparticles, films, tubes, scaffolds, gels, and fibers. The polymeric forms include, but are not limited to, solid polymers, semisolid polymers, hydrogels, and liquid polymers. The physical and chemical properties include the composition of the polymers, concentration of the functional groups, degradation rate, molecular weight, glass transition temperature ($T_g$), self-assembly/self-aggregation properties and others.

In Example 1 discussed below, the PEG grafting density and backbone composition of the poly(TMCC-co-LA)-g-PEG-furan 1 copolymers (FIG. 4) were tuned to design micro/nanoparticles with controlled particle size, critical aggregation concentrations (CACs), and furan concentration on the surface (Example 2). The molar ratio between TMCC and LA segments in the copolymer backbone was adjusted by the feed ratio of the two monomers. The PEG grafting density was well controlled by the initial feed ratio of PEG/poly (TMCC-co-LA) during the synthesis (Table 1). For the non-PEG-containing furan-substituted poly(allylTMC-co-LA) 2 (FIG. 5) and poly(furfurylTMC-co-LA) 3 (FIG. 6), the molecular weight, $T_g$ and furan content of the copolymers were controlled by the feed ratio of the two monomers during the synthesis (Table 2 and Table 3). The adjustable physical/chemical properties allow for the design of various polymeric carriers, such as polymeric films and polymeric microparticles and nanoparticles with defined requirements.

Figure 11:
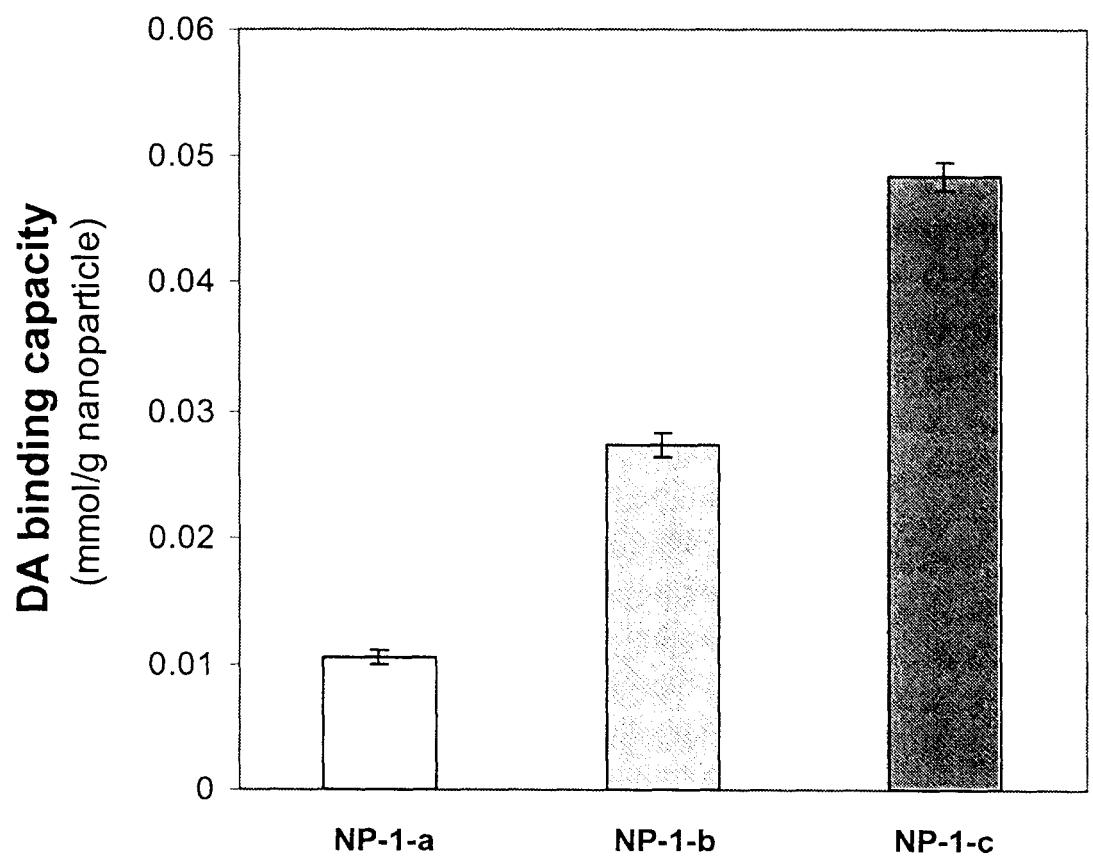
FIG. 11 shows the copolymer composition dependence of the Diels-Alder binding capacity of the nanoparticles.
Figure 13:
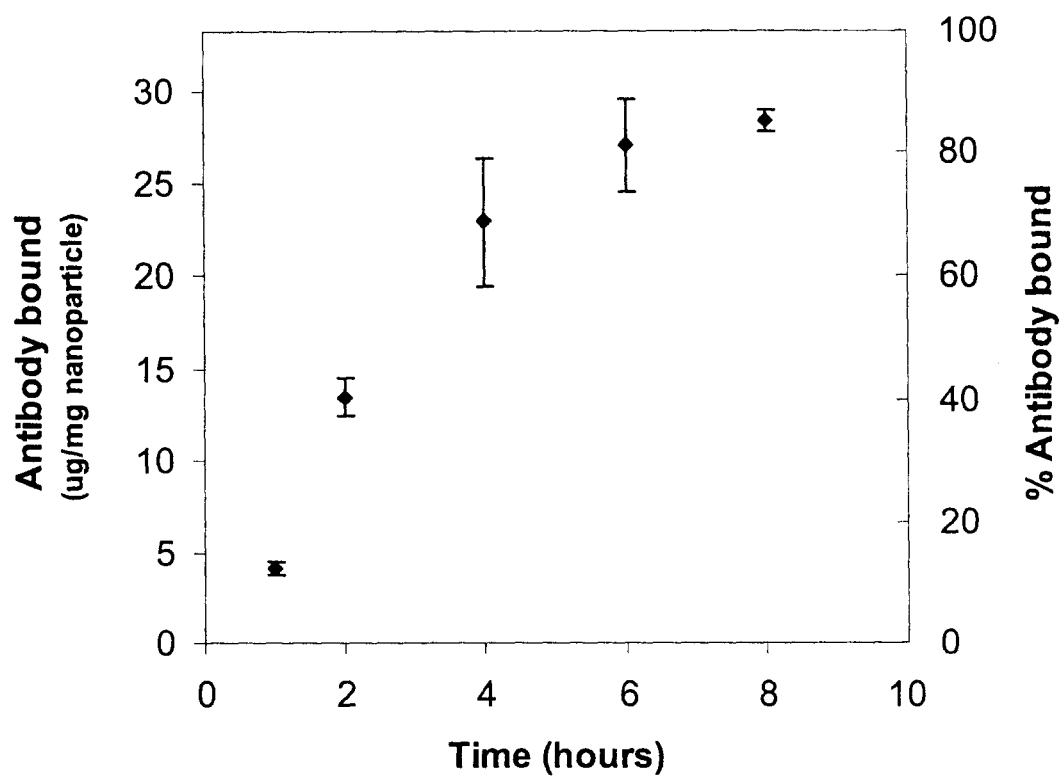
FIG. 13 shows the representative time-dependence of binding anti-bovine IgG immuno-nanoparticle to a bovine IgG-immobilized ELISA plate.
Figure 15:
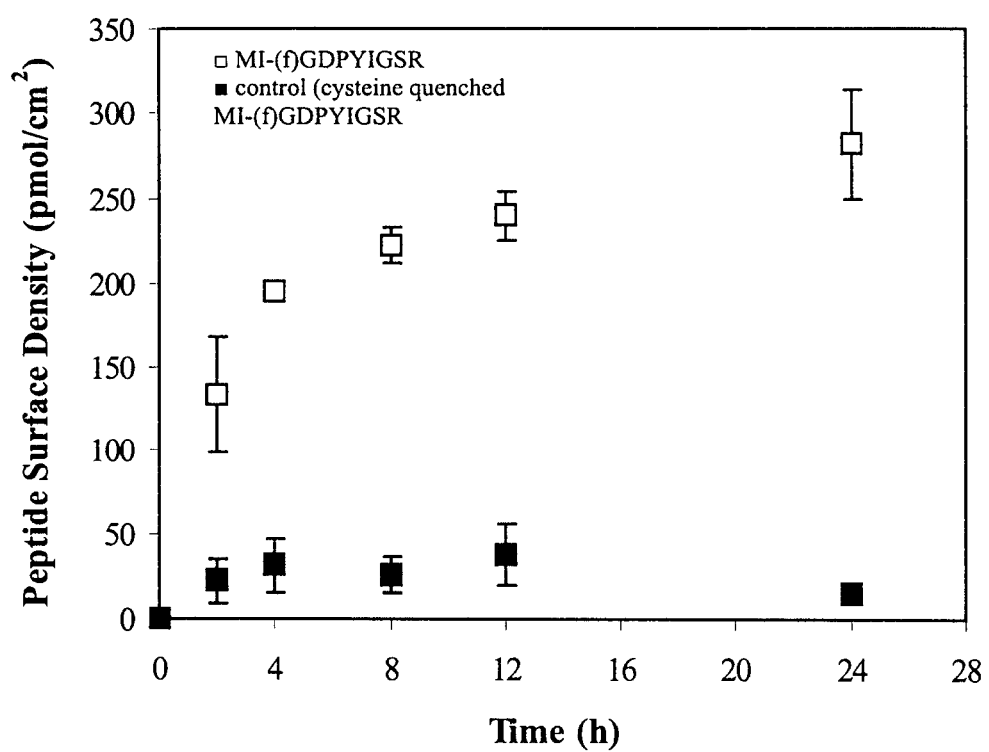
FIG. 15 shows the reaction time dependence of the peptide density on the surface of the furan-substituted poly(allylTMC-co-LA) polymer film.
Figure 16:
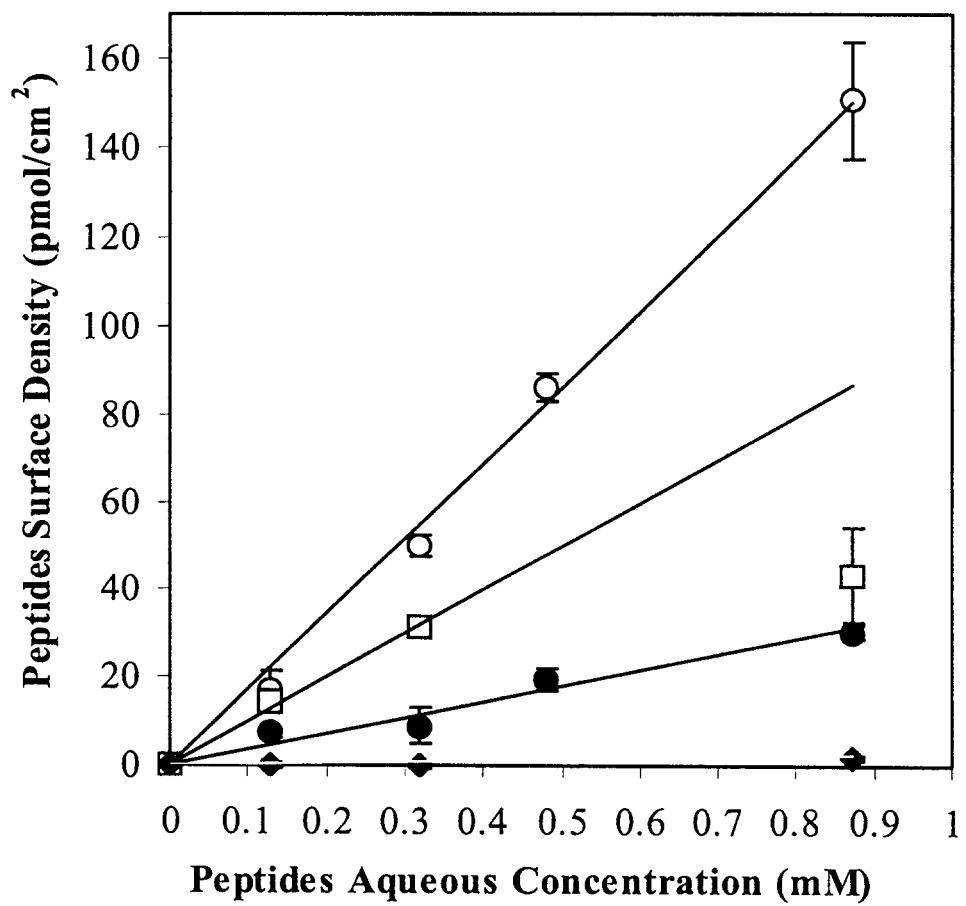
FIG. 16 shows the effects of peptide aqueous concentration on peptide surface density.

The polymer design in this invention also provides for an unexpected degree of control over the type and concentration of the functional groups in the polymers. This directly leads to control over the type and density of the biomolecules immobilized on the polymeric carriers. In Example 1, the presence of furan functional groups on poly(TMCC-co-LA)-g-PEG-furan 1, furan-substituted poly(allylTMC-co-LA)-furan 2, and poly(furfurylTMC-co-LA) 3 allows for the immobilization of maleimide-modified biomolecules (FIG. 13, FIG. 15 and FIG. 16). The concentration of furan is adjusted to control the density of biomolecules immobilized on the polymeric carriers (Table 1, Table 2 and Table 3). It is anticipated that the adjustable furan concentration controls the level of biomolecule immobilization. The ways by which the copolymers were synthesized allows versatile functionalization. For instance, poly(TMCC-co-LA)-g-PEG-azide (or alkyne) or poly(TMCC-co-LA-g-PEG-furan (and alkyne) can be prepared through a method (FIG. 7 and FIG. 8) similar to the one used for the preparation of poly(TMCC-co-LA)-g-PEG-furan (FIG. 4) by using the bifunctional BocNH-PEG-azide or BocNH-PEG-alkyne. The furan (or azide or alkyne) concentration in the final copolymer can be adjusted by the feed ratio of bifunctional PEG segments and poly(TMCC-co-LA) backbone segments (Table 1). In Example 2, the number of furan functional groups available on the nanoparticles is well controlled by the PEG grafting density of the copolymers (FIG. 11). A larger number of available furan groups indicates a greater capacity to bind with maleimide-containing species by Diels-Alder chemistry (defined Diels-Alder binding capacity in Example 2).

Additionally, the presence of both diene and alkyne functional groups on the polymeric carriers allows for the immobilization of biomolecules functionalized with reactive maleimide and azide, respectively. In Example 1, the synthesis of poly(TMCC-co-LA)-g-PEG-diene/alkyne, bearing two types of functional group on the same copolymer (FIG. 8), allows for the immobilization of two types of biomolecules on one polymeric carrier. The adjustable concentrations of diene and alkyne groups are used to control the density of the two biomolecules. Thus, the polymers may be functionalized with dienes, dienophiles, azides and alkynes, and biomolecules can be functionalized with all of these types as well.

The modification of biomolecules to introduce the required functional groups employs specific modification techniques that efficiently preserve specific bioactivity. In Example 3, the modification of the Fc portion of the antibodies leaves the Fab portion, which is responsible for antigen binding, undisturbed (Hermanson, G. T. Bioconjugate Techniques. Academic Press, 1996, pp 235-237). This modification technique is efficient, resulting in 2.3 maleimide groups per antibody molecule and preserving at least 72±14% of the specific bioactivity.

Herein, the terms biomolecules and therapeutic molecules refer to nearly every major group of natural compounds: nucleic acids (DNA, cDNA, RNA, and PNA), proteins (including but not limited to antibodies, antibody fragments, enzymes, ligands, receptors, viral vectors, and viruses), small molecules (such as polypeptides, peptides, amino acids, metabolites and drugs), and other biomolecules (such as vitamins, antibiotics, hormones, phage or even entire cells). The terms biomolecules and therapeutic molecules also include synthetic molecules that have biological effects. Useful drugs to be incorporated include Herceptin®, IL-2, and doxorubicin but it will be understood that any therapeutic drug may be encapsulated. In addition, molecules of no therapeutic value themselves may be bound to the particles or encapsulated for therapeutic purposes nevertheless, for example to deliver a radioactive or fluorescent marker to a particular site in a biological system (e.g. an animal or human) so that the combination of functionalized polymer and molecule are still considered to be for therapeutic delivery of a molecule.

The highly facile chemistry described in this invention proceeds with unexpected efficiency in buffered aqueous solutions with appropriate pH values. The Diels-Alder cycloaddition and Huisgen 1,3-dipolar cycloaddition (preferably Cu(I)-catalyzed) between small molecules both proceed rapidly to completion and tend to be highly selective for a single product. In this invention, although steric hindrance from the polymer chains is present and could be expected to complicate interaction with functional groups on the biomolecules due to their uneven distribution, chemical reaction between the polymers and biomolecules nonetheless proceeded with unexpected rapidity and efficiency within several hours (FIG. 13, FIG. 15 and FIG. 16). In Example 4, incubation of nanoparticles (self-aggregated from poly(TMCC-co-LA)-g-PEG-furan-1-b) with maleimide-modified antibodies at 37° C. achieved an unexpectedly high coupling efficiency of greater than 80% after 6 h, corresponding to 27.0 µg of antibody bound per mg of nanoparticle. The preservation of the specific bioactivity of the nanoparticle-bound antibody during the coupling procedure is essential for active drug targeting. The highly selective Diels-Alder antibody-coupling reaction occurs under very mild conditions with minimal impact on the bioactivity of the antibodies. This is also confirmed by the ELISA results (FIG. 13), which show that reaction time can be used to control the extent of antibody immobilization onto the nanoparticles, and that antigen-binding ability is maintained even after prolonged reaction times. In Example 4, the study of the effect of interfacial Diels-Alder reaction time on peptide surface density on furan functionalized polymer surfaces (prepared from furan-substituted poly (allylTMC-co-LA)) demonstrated that the peptide surface density increased dramatically within the first 4 h of reaction and then tended to reach a plateau between 4 and 24 h (FIG. 15). The highest surface density of 282±32 pmol/cm$^2$ was determined after 24 h of reaction.

Figure 14:
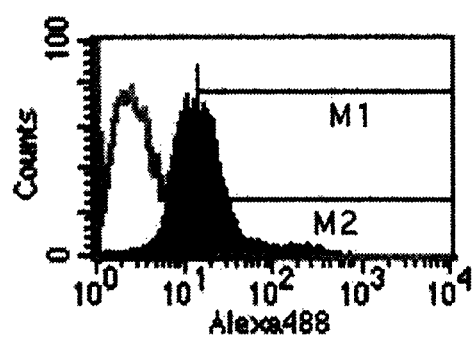
FIG. 14 shows the flow cytometry results which demonstrate anti-HER2 immuno-nanoparticles binding with HER2-overexpressed breast cancer cell SKBR3.
Figure 14:
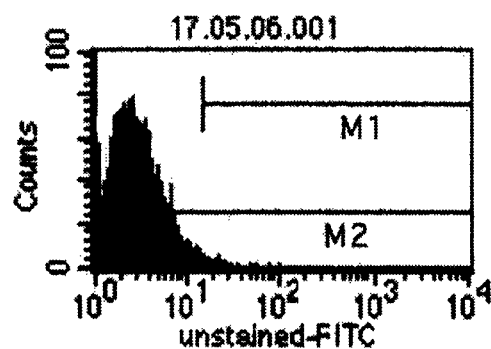
Figure 14:
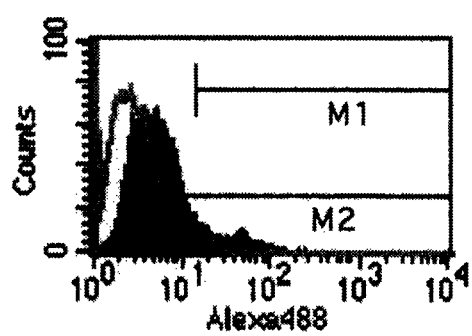
Figure 14:
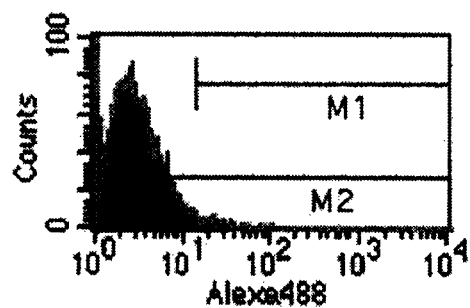

The highly efficient chemistry described in this invention for covalently binding the molecule of interest to the polymer particles proceeds under mild conditions with minimal impact on the bioactivity of the biomolecules coupled to the particles. In Example 4, the anti-bovine IgG immuno-nanoparticle prepared by the Diels-Alder cycloaddition was capable of binding with bovine IgG coated ELISA plates. The antigen-binding ability was maintained even after prolonged reaction times. The successful binding of anti-HER2 immuno-nanoparticles to HER2-overexpressing SKBR3 cancer cells further demonstrated that the specific antigen binding ability was preserved after the antibody coupling (FIG. 14).

Figure 9:
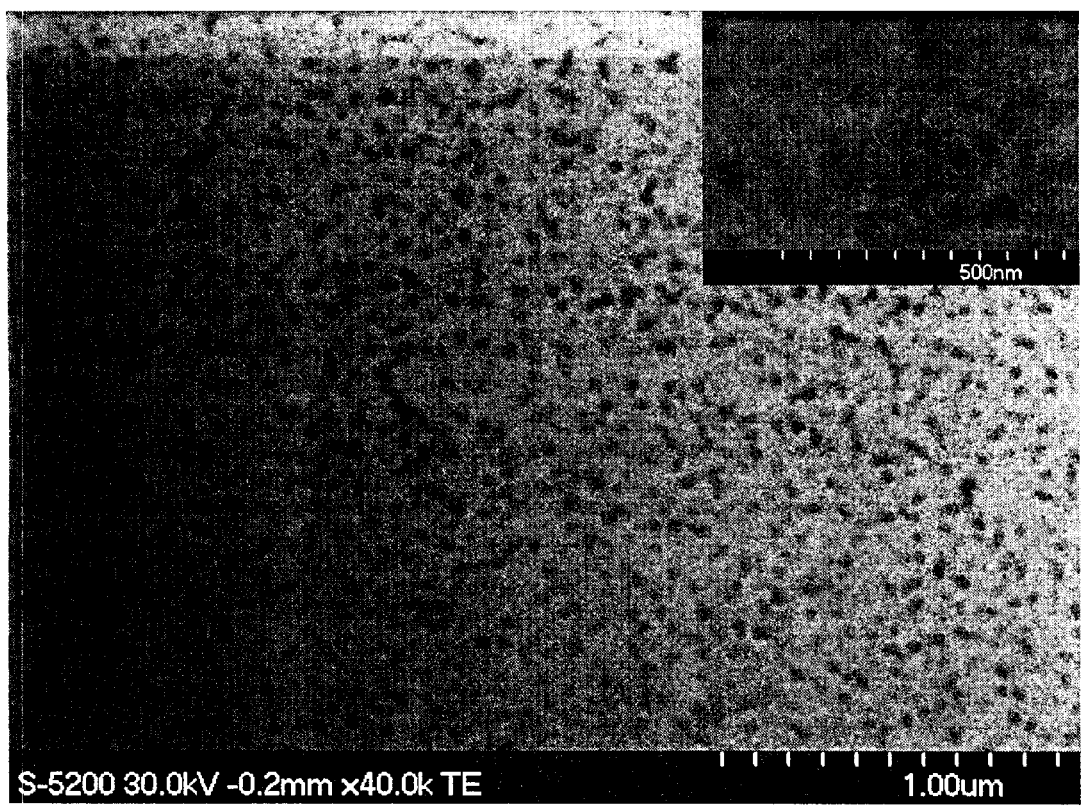
FIG. 9 shows a representative STEM image of self-aggregated nanoparticles from poly(TMCC-co-LA)-g-PEG-furan copolymer.

The polymer design in this invention provides a method to prepare novel particle systems for targeted and controlled therapeutic delivery. Self-aggregation of amphiphilic copolymers leads to the formation of microscopic or nanoscopic particles by intra- or intermolecular association (FIG. 9). The amphiphilic nature of the poly(TMCC-co-LA)-g-PEG-furan copolymers, composed of the hydrophobic poly(TMCC-co-LA) backbone and hydrophilic PEG chains, drives the formation of particle structure when organic solutions of the polymers are dialyzed against water. Long flexible PEG chains comprise the nanoparticle surface and sterically stabilize the nanoparticles. This is important for applications in cancer therapy, where nanoparticles may be injected intravenously and reach the target tissue through the "leaky" vasculature associated with cancerous tissue. This "passive targeting" is enhanced by the PEG corona of the nanoparticle drug delivery system, which is expected to provide prolonged blood circulation times. Functional groups which are located on the terminus of the PEG chains are available on the surface of the particles for at least one of Diels-Alder cycloaddition or 1,3-dipolar Huisgen cycloaddition chemistry after self-aggregation. Unexpectedly, the inner hydrophobic core of poly (TMCC-co-LA) can host both hydrophobic drugs and hydrophilic drugs (such as protein-based drugs) due to the hydrophobicity of the inner core and the presence of carboxyl groups on the copolymer backbone, respectively. In Example 2, hydrophobic anticancer drug Doxorubicin and protein drug Interleukin-2 were encapsulated within the nanoparticle by a similar process of dialysis (Table 5 and Table 6).

Surprisingly, the structure and property of the micro/nanoparticles can be finely tuned by controlling the composition of the copolymers. In Example 2, the size of the particles is shown to be dependent on the composition of the copolymers (Table 4). The size (and degree of PEGylation) of the nanoparticles is expected to predominantly influence their blood circulation time and organ distribution. Evidence in both experimental animals and humans has shown that nanoparticles which are less than 200 nm in size are more resistant to reticuloendothelial system (RES) clearance and can extravasate in specific cancers. As the hydrophobic polymer domain plays an essential role in self-aggregation behavior, the composition of the copolymer backbone largely determined the size of the nanoparticles (Table 4): Larger numbers of carboxylic acid substituents in the hydrophobic segments result in increased steric and electrostatic repulsion along the polymer chains, leading to larger particle size of the self-aggregated nanoparticles. Moreover, the presence of carboxylic acid substituents in the copolymers significantly influences the hydrophobicity of the backbone, and so the effective diameters of the self-aggregated nanoparticles show sensitivity to pH and ionic strength (Table 4), suggesting that these copolymer nanoparticles can be used as stimuli-responsive drug delivery vehicles. The thermodynamic stability (CAC in FIG. 10) results indicate that the self-aggregated structure will be stable at concentrations as low as $10^{-8}$ M, providing limited dissociation when used as a drug delivery vehicle for in vivo applications. It is noteworthy that the CAC values for these poly(TMCC-co-LA)-g-PEG-furan graft copolymers are significantly lower (i.e., $10^{-8}$ M or 1 to 5 μg/ml) than those reported for synthetic amphiphilic polymers intended for drug delivery (i.e., $10^{-7}$ to $10^{-2}$ M or 10 to 1000 μg/ml, depending on the polymer molar mass). The inventors contemplate that, taking advantage of both passive and active targeting, the high aggregate stability in the system according to the present invention will lead to a highly efficient drug delivery vehicle for intravenous drug delivery.

(TMCC-co-LA) backbone. $^1$H NMR data (CDCl$_3$, 300 MHz): δ 1.38-1.48 ppm, (bm, CH$_3$ protons of the poly (TMCC-co-LA) backbone), 3.45-3.52 ppm (bs, CH$_2$ protons of the PEG grafts), 5.05-5.25 ppm (bm, CH$_2$ protons of the poly(TMCC-co-LA) backbone). The final poly(TMCC-co-LA)-g-PEG-furan copolymers have an adjustable backbone composition (which has impact on the size of the nanoparticle self-aggregated from the copolymer) and controlled PEG grafting density, the average PEG number per copolymer backbone (which has impact on the ability of the nanoparticle to bind with biomolecules by DA chemistry). The characterization of the copolymers is shown in Table 1.

TABLE 1

Characterization of poly(TMCC-co-LA)-g-PEG-furan graft copolymers 1

| Graft copolymers | Feed mass ratio Poly(TMCC-co-LA):PEG-furan[3] | Feed molar ratio[4] Poly(TMCC-co-LA):PEG-furan | PEG-furan grafts/ copolymer chain[5] | Molecular weight (Mn) (kDa)[5] |
|---|---|---|---|---|
| Poly(TMCC-co-LA)-g-PEG-furan-1-a[1] | 1:0.25 | 1:1.5 | 0.63 | 22.9 |
| Poly(TMCC-co-LA)-g-PEG-furan-1-b[1] | 1:0.5 | 1:3.0 | 0.99 | 24.2 |
| Poly(TMCC-co-LA)-g-PEG-furan-1-c[1] | 1:1 | 1:6.0 | 1.64 | 26.4 |
| Poly(TMCC-co-LA)-g-PEG-furan-2-b[2] | 1:0.5 | 1:2.3 | 1.00 | 19.2 |

[1]Synthesized from poly(TMCC-co-LA)-1, Mn = 20.8 kDa and PDI = 2.5 as determined by GPC; Molar ratio of TMC = 6.5% as estimated from $^1$H NMR;
[2]Synthesized from poly(TMCC-co-LA)-2, Mn = 15.8 kDa and PDI = 2.3 as determined by GPC; Molar ratio of TMC = 13.0% as estimated from $^1$H NMR
[3]PEG: Mw = 3.4 kDa, Mn = 3.4 kDa from manufacturer;
[4]Molar ratio based on Mn of poly(TMCC-co-LA) and PEG;
[5]Estimated from $^1$H NMR and calculated based on Mn of poly(TMCC-co-LA) and PEG The invention will now be illustrated with respect to the exemplary examples which are not to be interpreted to limiting in any way.

EXAMPLES

Example 1

Synthesis of Functionalized Biodegradable Polymers

Figure 5:
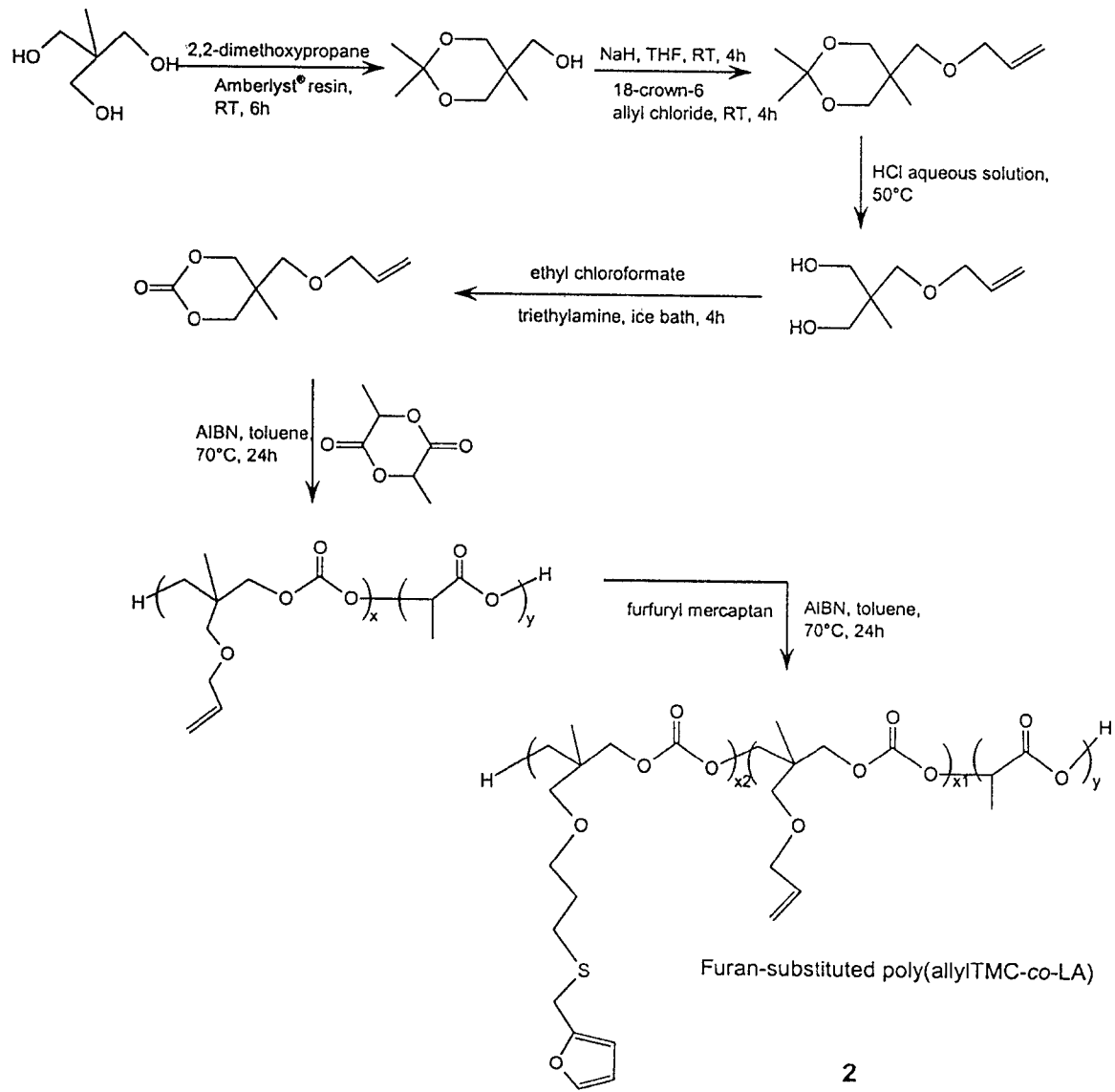
FIG. 5 shows an exemplary synthesis of furan-substituted poly(allylTMC-co-LA) copolymer.

The amphiphilic biodegradable copolymer, poly(2-methyl-2-carboxytrimethylene carbonate-co-D,L-lactide)-graft-poly(ethylene glycol)-furan (poly(TMCC-co-LA)-g-PEG-furan) 1, comprising a hydrophobic backbone of poly (TMCC-co-LA) and a hydrophilic graft of furan-terminated PEG, was synthesized as shown in FIG. 3 and FIG. 4. The carboxylic acid group of 2,2-bis(hydroxymethyl)propionic acid was protected by a benzyl group to yield benzyl 2,2-bis (hydroxymethyl)propionate, which was then condensed with ethyl chloroformate to form a cyclic carbonate monomer 5-methyl-5-benzyloxycarbonyl-1,3-dioxan-2-one. The resulting cyclic carbonate monomer was co-polymerized with D,L-lactide by ring-opening polymerization with tin octanoate in a bulk melt to produce the benzyl-protected poly(TMCC-co-LA). The benzyl group was removed, yielding native poly(TMCC-co-LA). $^1$H NMR (CDCl$_3$, 300 MHz): δ 1.20-1.30 ppm (bm, CH$_3$ protons of the TMC segments), 1.35-1.55 ppm (bm, CH$_3$ protons of the LA segments), 4.10-4.30 ppm (bm, CH$_2$ protons of the TMC segments), 5.05-5.25 ppm (bm, CH protons of the LA segments), 7.35 ppm (bm, Ar). In FIG. 4, BocNH-PEG-NHS was coupled with furfurylamine to yield BocNH-PEG-furan. The Boc-protected amine was then deprotected with trifluoroacetic acid and coupled to the carboxyl groups of the poly Furan-substituted poly(allylTMC-co-LA) copolymers 2 were synthesized as shown in FIG. 5. These copolymers were derived from poly(allylTMC-co-LA) copolymers by addition of the reactive thiol group of furfuryl mercaptan to the pendant allyl groups of the copolymers. $^1$H NMR (CDCl$_3$) of poly(allylTMC-co-LA) copolymer: δ 1.0 ppm (CH$_3$ protons from allyl), 1.55 (m, CH$_3$ protons from lactide), 3.32 (d, —CCH$_2$OCH2), 3.93 (d, —OCH$_2$—CH=CH$_2$), 4.10 (s, —CH$_2$CCH$_2$—), 5.13~5.30 (m, —OCH$_2$CH=CH2 and —CHCH3), 5.7-5.9 (m, —OCH$_2$CH=CH$_2$). The final furan-substituted poly(allylTMC-co-LA) copolymers have controlled furan composition and physical properties. The characterization of furan-substituted poly(allylTMC-co-LA) before and after furan bulk modification is shown in Table 2.

TABLE 2

Characterization of poly(allylTMC-co-LA) copolymers 2

| Copolymer | Allyl content (mol %)[a] | Furan content (mol %)[a] | $T_g$ (° C.) | $M_w{}^b$ (g/mol) | $Mn^b$ (g/mol) | PDI[b] |
|---|---|---|---|---|---|---|
| Poly(allylTMC-co-LA)-1-b[1] | 12.5 | 0 | 21 | 27,500 | 13,920 | 1.97 |
| Furan-substituted Poly(allylTMC-co-LA)-1-a[2] | 8.5 | 4 | 23 | 36,900 | 15,100 | 2.45 |

TABLE 2-continued

Characterization of poly(allylTMC-co-LA) copolymers 2

| Copolymer | Allyl content (mol %)[a] | Furan content (mol %)[a] | $T_g$ (° C.) | $M_w$[b] (g/mol) | $Mn$[b] (g/mol) | PDI[b] |
|---|---|---|---|---|---|---|
| Furan-substituted Poly(allylTMC-co-LA)-2-b[1] | 20.0 | 0 | 12 | 22,200 | 12,100 | 1.83 |
| Poly(allylTMC-co-LA)-2-a[1] | 12.2 | 7.8 | 13 | 40,200 | 15,600 | 2.57 |

Figure 6:
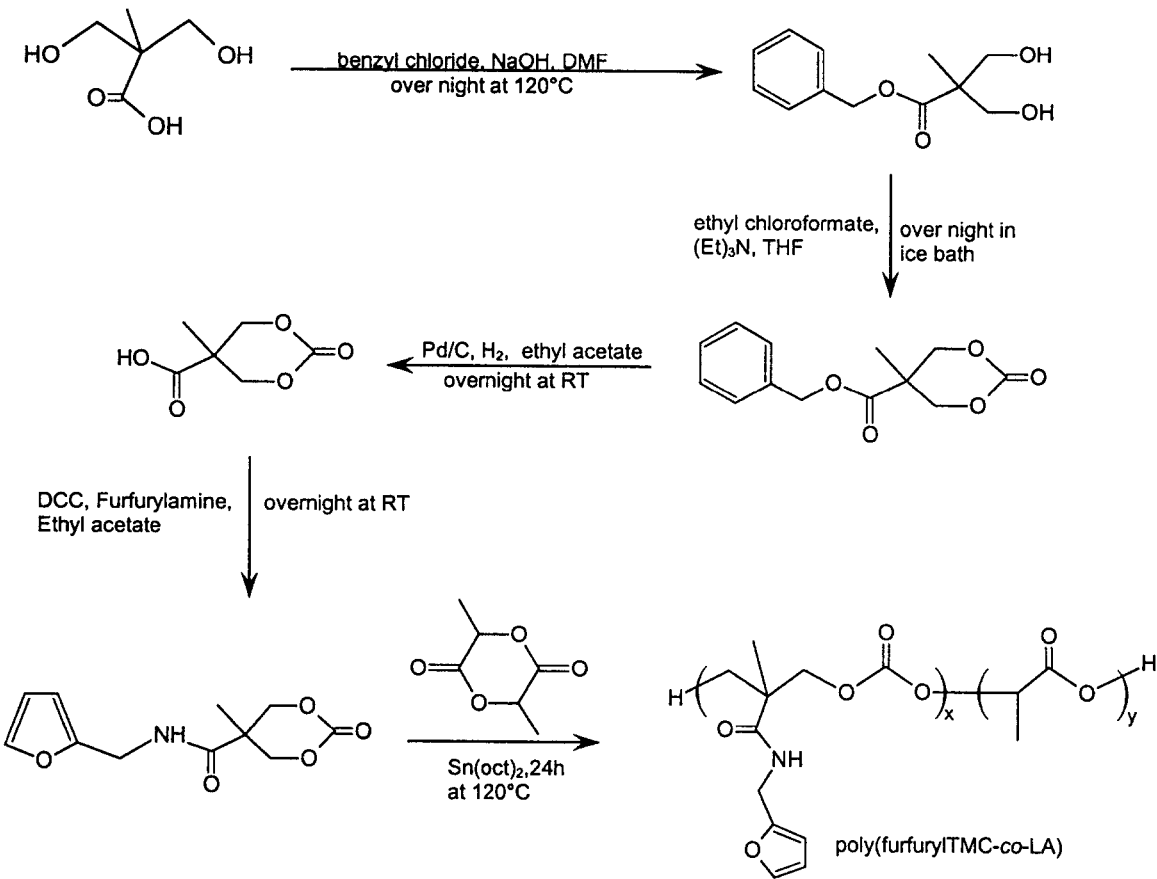
FIG. 6 shows an exemplary synthesis of poly(furfurylTMC-co-LA) copolymer.

[a]Determined from $^1$H NMR
[b]Determined from GPC
[1]Before furan bulk modification
[2]After furan bulk modification Furan-containing poly(furfurylTMC-co-LA) copolymers 3 were synthesized as shown in FIG. 6. The carboxylic acid group of 2,2-bis(hydroxymethyl)propionic acid was protected by a benzyl group and then the diol reacted with ethyl chloroformate to yield 5-methyl-5-benzyloxycarbonyl-1,3-dioxan-2-one prior to deprotection of the benzyl ester to yield 5-methyl-5-carboxy-1,3-dioxan-2-one. The 5-methyl-5-carboxy-1,3-dioxan-2-one reacted with furfurylamine to yield a novel furan-containing monomer 5-furfurylamide-5-methyl-1,3-dioxane-2-one. $^1$H NMR (CDCl$_3$) δ 1.33 (s, 3H, CH$_3$), 4.20 (d, 6H, CH$_2$O), 4.45 (d, 2H, CH$_2$O), 6.22 (m, 1H, furan), 6.32 (m, 1H, furan), 6.65 (m, 1H, NHCO), 7.35 (m, 1H, furan). The furan-containing monomer was copolymerized with D,L-lactide to yield poly(furfurylTMC-co-LA) copolymers. The ratio of two segments and furan concentration in the copolymers can be tuned to design various copolymers with different physical/chemical properties. The characterization of poly(furfurylTMC-co-LA) is shown in Table 3.

TABLE 3

Characterization of poly(furfurylTMC-co-LA) copolymers 3

| Copolymer | Furan content (mol %)[a] | $T_g$ (° C.) | $Mw$[b] (g/mol) | $Mn$[b] (g/mol) | PDI[b] |
|---|---|---|---|---|---|
| Poly(furfurylTMC-co-LA)-2 | 2.0 | 44 | 21,200 | 10,200 | 2.08 |
| Poly(furfurylTMC-co-LA)-10 | 10.0 | 47 | 10,100 | 4,770 | 2.12 |

[a]Estimated from $^1$H NMR.
[b]Determined from GPC.

Alkyne (or azide)-functionalized poly(TMCC-co-LA)-g-PEG copolymers were synthesized as shown in FIG. 7. The NHS end of BocNH-PEG-NHS was coupled with propargylamine (or azido-PEG-amine (n=8)) to introduce alkyne or azide functional groups, respectively. The BocNH end of the PEG chains was deprotected with trifluoroacetic acid followed by coupling to carboxyl groups along the poly(TMCC-co-LA) backbone.

Example 2

Preparation of Nanoparticles

Self-aggregated nanoparticles from copolymers 1 (FIG. 4) were prepared by a dialysis process. Briefly, 5 mg/ml poly(TMCC-co-LA)-g-PEG-furan copolymer solution in dimethyl sulfoxide (DMSO)/borate buffer (90:10 vol. %) was dialyzed against distilled water using a dialysis membrane with a molecular weight cut-off (MWCO) of 12-14 kg/mol at room temperature (RT) for 24 h. The distilled water was replaced every two hours for the first 8 h. The resulting particle solution was centrifuged at 4000 rpm for 5 min to remove the aggregates. The characterization of the nanoparticles is shown in Table 4 and FIGS. 9 to 11.

TABLE 4

The effective diameters of self-aggregated nanoparticles

| | Effective diameters in various aqueous environments effective diameter(nm) (polydispersity*) | | |
|---|---|---|---|
| Nanoparticle samples | pH 7.4 (PBS buffer 10 mM) | pH 6.8 (HEPES buffer 10 mM) | Distilled water |
| NP-1-a[1] | 49.7 (0.201) | 48.7 (0.005) | 43.9 (0.152) |
| NP-1-b[2] | 46.5 (0.029) | 42.8 (0.163) | 38.2 (0.005) |
| NP-1-c[3] | 46.0 (0.261) | 44.3 (0.005) | 35.2 (0.138) |
| NP-2-b[4] | 111.7 (0.128) | 98.1 (0.303) | 84.8 (0.279) |

[1,2,3]Nanoparticles self-aggregated from copolymer poly(TMCC-co-LA)-g-PEG-furan 1-a, 1-b, and 1-c, respectively. The copolymers have backbones of 6.5% TMCC content with increased PEG grafting density.
[4]Nanoparticles self-aggregated from copolymer 2-b (backbone of 13.0% TMCC content).
*Polydispersity index is the measure of the homogeneity of a dispersion, ranging from 0.0 (monodisperse) to 1.0 (very heterogeneous).

Figures 10A, 10B:
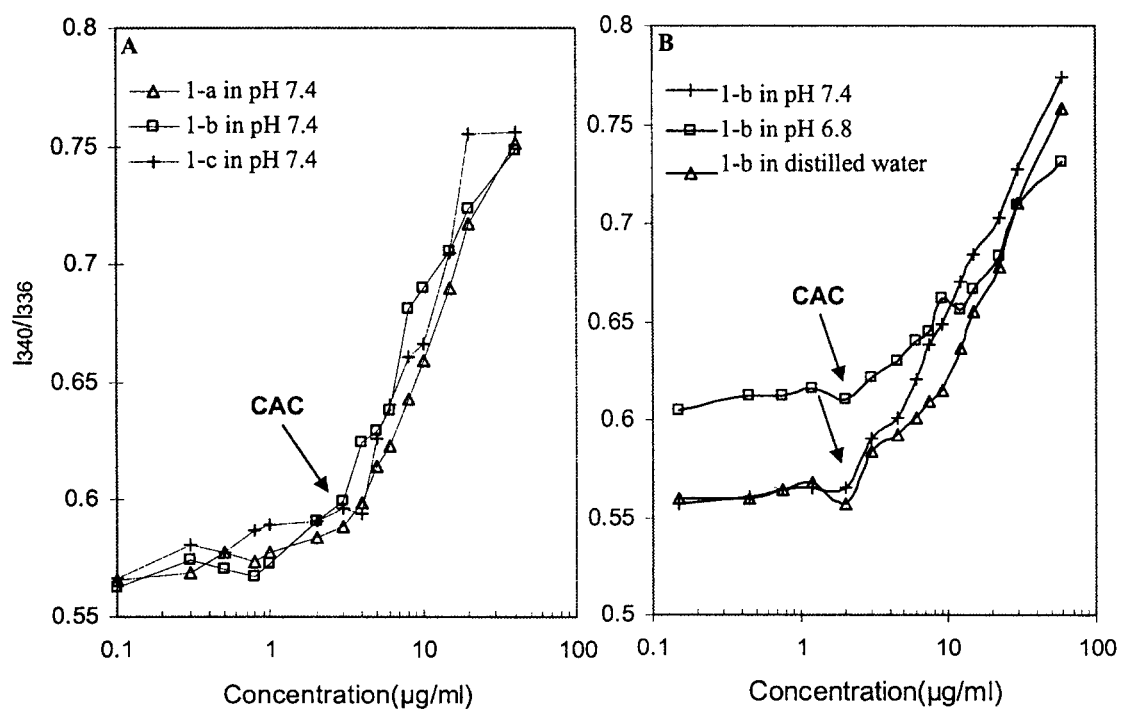
FIG. 10 shows the determination of CAC values of the poly(TMCC-co-LA)-g-PEG graft copolymers.

The STEM image shown in FIG. 9 demonstrates the successful formation of a core-shell structure of the self-aggregating system. Each nanoparticle appears as a dark spot corresponding to the hydrophobic centre core, surrounded by a gray corona originating from the hydrophilic PEG graft. FIG. 10 is the determination of CAC values of the poly(TMCC-co-LA)-g-PEG graft copolymers: when exposed to amphiphilic copolymer solution, pyrene molecules preferably partition into the hydrophobic microdomains of self-aggregates, which results in different photophysical characteristics. The CACs were determined by taking the crossover point of the curve of the intensity ratio (340 nm/336 nm) from pyrene excitation spectra versus concentration of polymer in aqueous solutions. FIG. 10A is the determination of CACs of poly(TMCC-co-LA)-g-PEG-furan-1-a, poly(TMCC-co-LA)-g-PEG-furan-1-b and poly(TMCC-co-LA)-g-PEG-furan-1-c (backbone of 6.5% TMC content with increased PEG grafting density); FIG. 10B is the determination of CACs of poly(TMCC-co-LA)-g-PEG-furan-1-b in different aqueous environments.

The critical aggregation concentration (CAC) values of the copolymers fall into the range of 1 to 5 μg/ml for the graft copolymers with different PEG grafting density, even in different aqueous environments. These results indicate that the self-aggregated structure will be stable at concentrations as low as $10^{-8}$ M, providing limited dissociation when used as a drug delivery vehicle for in vivo applications. The Diels-Alder binding capacity of the nanoparticles was defined as the maximum number of maleimide-modified molecules bound per gram of nanoparticle, without considering the steric hindrance between bound molecules.

FIG. 11 shows the Diels-Alder binding capacity of the nanoparticles is a function of PEG-furan grafting density on the copolymers. For example, the nanoparticles from copolymer poly(TMCC-co-LA)-g-PEG-furan-1-c (Table 1) with 1.64 PEG grafts per copolymer chain had the highest DA binding capacity, at 0.05 mmol/g copolymer nanoparticle. The results in Table 5 and Table 6 describe the drug encapsulation properties of the nanoparticles. Both small-molecule hydrophobic drugs and large protein drugs can be successfully encapsulated with the nanoparticles by dialysis. The drug loading of DOX before (1.41±0.04 μg/mg nanoparticle) and after (1.33±0.01 μg/mg nanoparticle) antibody coupling indicates that the Diels-Alder immobilization reaction did not greatly change the drug loading (Table 5). The effective diameter of the immuno-nanoparticles with encapsulated DOX (103.5 nm with a polydispersity of 0.182) was higher than that of nanoparticles without bound antibody (81.6 nm with a polydispersity of 0.311). Thus coupling the antibody on the surface of the nanoparticle increased its hydrodynamic radius. The presence and concentration of carboxylic acid groups on the copolymer backbone play an important role for Interleukin-2 encapsulation. The driving force for protein encapsulation was likely the hydrogen-bonding and electrostatic interactions between the protein and the charged copolymer backbone.

TABLE 5

Characterization of hydrophobic drug encapsulation of copolymer nanoparticles[a]

| Type of drugs | Drug content | |
|---|---|---|
| | Before antibody conjugation | After antibody conjugation |
| Doxorubicin[b] (Hydrophobic drug) | 1.41 ± 0.04 μg/mg nanoparticle | 1.33 ± 0.01 μg/mg nanoparticle |

[a]The Doxorubicin-encapsulated nanoparticles were prepared by a similar process as the blank nanoparticles. The copolymer employed here was poly(TMCC-co-LA)-g-PEG-furan-1-b;.
[b]The freeze-dried nanoparticles were dissolved in DMF and the doxorubicin concentration was determined with a fluorescent microplate reader operating at an excitation wavelength of 475 nm and emission wavelength of 580 nm.

TABLE 6

Characterization of protein drug encapsulation of copolymer nanoparticles

| Nanoparticles[a] | Drug content[c] Interleukin-2 (ng)/ copolymer (mg) | Encapsulation Efficiency drug encapsulated/ drug feed (%) |
|---|---|---|
| NP-1-a[b] | 63.9 ± 28.1 | 9.6 ± 4.2 |
| NP-1-b[b] | 42.0 ± 9.0 | 6.3 ± 1.3 |
| NP-1-c[b] | 107.5 ± 14.1 | 16.1 ± 2.1 |

[a]The protein-encapsulated nanoparticles were prepared as a similar process as the blank nanoparticles.
[b]NP-1-a was prepared from the copolymer poly(TMCC-co-LA)-g-PEG-furan-1-a; NP-1-b was prepared from the copolymer poly(TMCC-co-LA)-g-PEG-furan-1-b; NP-1-c was prepared from the copolymer poly(TMCC-co-LA)-g-PEG-furan-1-c;
[c]The freeze-dried nanoparticles were dissolved in dichloromethane (DCM) and interleukin-2 was extracted with PB buffer of pH 7.2 with SDS (1%). The concentration of interleukin-2 was determined by enzyme-linked immunosorbent assay (ELISA).

Example 3

Modification of Biomolecules

Maleimide-modified rabbit anti-bovine IgG antibody 4 (Mal-Ab) was prepared by oxidation of polysaccharide residues on the Fc portion with sodium periodate followed by conjugation with maleimide-containing molecule 4-(4-N-maleimidophenyl)butyric acid hydrazide (MPBH) (Hermanson, G. T. Bioconjugate techniques. Academic Press, c1996, 235-237). 100 μl of sodium periodate solution (0.1 M in 100 mM acetate buffer of pH 5.5) was added into 0.5 ml of antibody solution (2.0 mg/ml in distilled water). The reaction solution was protected from light and incubated at RT for 30 min. The oxidized antibody was purified immediately by passing the reaction solution through a Sephadex G-25 column with 100 mM acetate buffer of pH 5.5. The concentration of oxidized antibody was determined by UV-VIS spectrometer. MPBH solution (5 mg/ml in DMSO) was added slowly into the oxidized antibody solution at a 20-times molar excess. The reaction solution was incubated at RT for 2 h, followed by adding 10 μl of 5 M sodium cyanoborohydride solution (prepared in 1 N NaOH) per millilitre reaction solution in a fume hood and reacting for 30 min at RT. The unreacted aldehyde sites were blocked by adding 50 μl of 1 M ethanolamine (in distilled water, pH 9.6 adjusted by HCl) per millilitre reaction solution. The reaction was incubated at RT for 30 min. The maleimide-modified antibody was purified immediately by passing the reaction solution through a Sephadex G-25 column with 50 mM MES buffer of pH 5.5. Based on an IgG-specific ELISA, the mean (±standard deviation) of 72±14% of the specific bioactivity of IgG is preserved after the site-specific modification of carbohydrate chains within the Fc region.

The number of maleimide residues per antibody molecule was determined indirectly by assaying the binding to Mal-Ab of a thiol-containing fluorescent probe, 5-((2-(and 3-)-S-(acetylmercapto)succinoyl)amino)fluorescein (SAMSA fluorescein). This experiment demonstrated that there was an average of 2.3 maleimide groups per antibody molecule.

Azide-modified rabbit anti-bovine IgG antibody was prepared using the method described above (oxidation followed by hydrazide conjugation) using a new heterobifunctional linking reagent, 4-azidomethylbenzoyl hydrazide (AMBH), in place of the MPBH. AMBH was prepared as follows: methyl 4-bromomethylbenzoate (1 mmol) was dissolved in a 0.5 M solution of sodium azide in DMSO (3 ml). The reaction mixture was stirred for two hours, poured into water, and extracted twice with ether. After washing with brine and drying over anhydrous magnesium sulfate, the ether solution was evaporated to give 88% of a clear oil (methyl 4-azidomethylbenzoate). This product (2.3 mmol) was dissolved in ethanol (10 ml) containing 4 ml of hydrazine hydrate. After heating at reflux for one hour, the reaction mixture was cooled to room temperature and then partially concentrated under reduced pressure, causing the precipitation of a white solid, which was filtered, washed with cold water, and dried, giving 50% of 4-azidomethylbenzoyl hydrazide. $^1$H NMR (DMSO-$d_6$): 9.78 (s, 1H), 7.84 (app d, 2H, 6.3 Hz), 7.43 (d, 2H, 8.4 Hz), 4.51 (app s, 4H).

Synthesis of maleimide-modified peptide N-(3-maleimidopropionyl)-N-(fluorescein)lysine-GDPGYIGSR (Mal-(f)GDPGYIGSR) 5 was performed on a solid-state peptide synthesizer on the 0.1 mmol scale. In general, the desired oligopeptide sequence, i.e. GDPGYIGSR (SEQ ID NO:1), was first synthesized on a 0.1 mmol scale on a peptide synthesizer without cleaving the side chain protecting groups. A fluorescein-labeled lysine derivative, N-Fmoc-N-(5/6-carboxyfluorescein)-L-lysine was added to the N-terminus. In a separate dried flask, 3-maleimidopropionic acid (1 mmol) was activated using dicyclohexylcarbodiimide (1 mmol) in dichloromethane (10 ml) for 30 min under nitrogen protection and a white precipitate was filtered. The filtrate was collected and reacted with the amine terminus of the peptide on the resin for 2 h. The resin was washed sequentially with dichloromethane, 2-propanol, and methanol before being dried under vacuum. The MI-(f)GDPGYIGSR was deprotected and cleaved from the resin using 95% aqueous trifluoroacetic acid (TFA; 2 h) and then lyophilized.

Example 4

Immobilization Reaction

Figure 12:
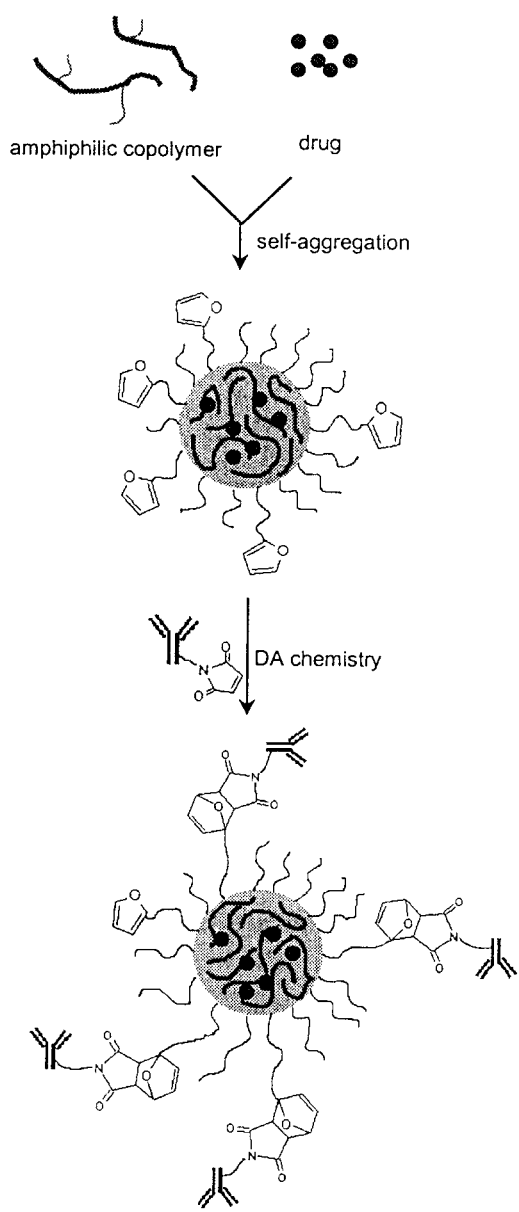
FIG. 12 shows a schematic presentation of the formation of immuno-nanoparticles by DA chemistry.

The Mal-Ab was immobilized on the surface of the poly (TMCC-co-LA)-g-PEG-furan nanoparticles by Diels-Alder cycloaddition as in the scheme shown in FIG. 12.

3.0 mg/ml copolymer nanoparticle solution in distilled water was mixed with the same volume of 0.1 mg/ml Mal-Ab 4 solution in 50 mM MES buffer of pH 5.5. The reaction solution was incubated under mild shaking at 37° C. for various time periods. The immuno-nanoparticles were purified by passing over a Sephacryl S-300HR column in PBS buffer of pH 7.4. The bound antibody was quantified by enzyme-linked immunosorbent assay (ELISA). The result is shown in FIG. 13, which demonstrates not only the successful coupling of the Mal-Ab with the nanoparticle but also the high efficiency of the DA chemistry. It is notable that a coupling efficiency of greater than 80% was achieved after 6 h of incubation, corresponding to 27.0 µg of antibody bound per mg of nanoparticle. The highly selective Diels-Alder antibody-binding reaction occurs under very mild conditions with minimal impact on the bioactivity of the antibodies. This is confirmed by the ELISA results, which show that reaction time can be used to control the extent of antibody immobilization onto the nanoparticles, and that antigen-binding ability is maintained even after prolonged reaction times. To demonstrate the binding of the immuno-nanoparticles (antibody-coupled nanoparticles) with the receptor-expressed cells, a monoclonal antibody Herceptin® was coupled with the nanoparticles using the procedure described above. Herceptin® antibodies specifically recognize and bind with the HER2 receptor, which is overexpressed on the surface of SKBR3 breast cancer cells. The flow cytometry results in FIG. 14 demonstrate that anti-HER2 immuno-nanoparticles successfully bound with SKBR3 breast cancer cells.

Mal-(f)GDPGYIGSR 5 was immobilized on the surface of films of the furan-substituted poly(allylTMC-co-LA) copolymer 2 by Diels-Alder cycloaddition as shown below:

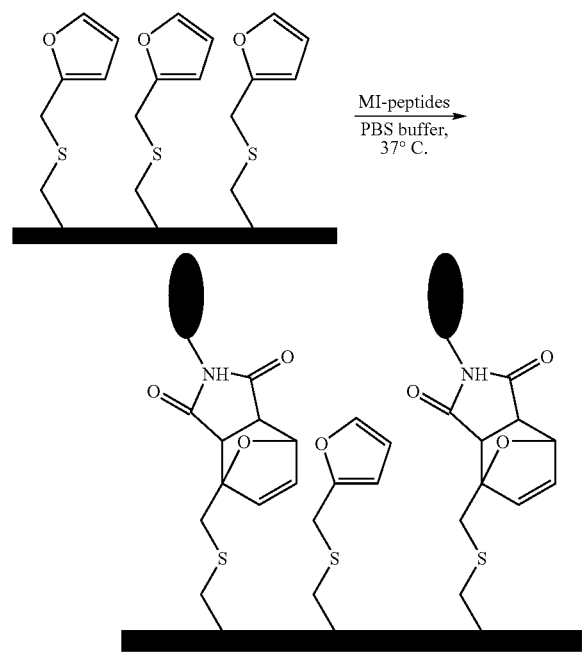

Polymeric films were prepared by a solution casting method. Briefly, a 2.5% copolymer solution in chloroform was prepared and filtered through a 0.22 µm filter. The solution was dropped onto circular glass slide surfaces (D=1.25 cm) and the solvent was evaporated slowly overnight to form thin films. All films were further dried under vacuum at 50° C. The furan-substituted poly(allylTMC-co-LA) copolymer film was immersed in $^{125}$I radiolabelled MI-(f)GDPGYIGSR solutions (0.87 mM in PBS buffer, pH=5.5). The reaction was carried out at 37° C. for 2~24 h. After washing the films extensively with water and then 0.01 M PBS buffer solution (pH=7.4), the films were further immersed into a 5% KI aqueous solution for 10 min to remove traces of free $^{125}$I residue on the surface before γ-counting. In control experiments, the maleimide groups of the peptide were quenched with L-cysteine and then the furan-substituted poly(allylTMC-co-LA) copolymer copolymer films were immersed in this solution to test the Diels-Alder reaction vs. adsorption. The results are shown in FIG. 15. The peptide surface density has a trend to reach a plateau between 8 and 24 h, with the highest surface density of 282±32 pmol/cm$^2$ after 24 h reaction time.

Mal-(f)GDPGYIGSR 5 was immobilized on the surface of films of the poly(furfurylTMC-co-LA) copolymer 3 by Diels-Alder cycloaddition as shown below:

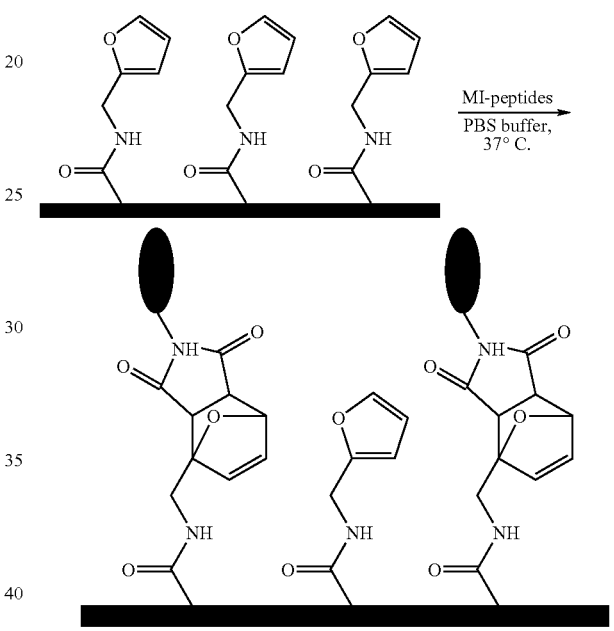

The effect of peptide aqueous concentrations on peptide surface density and physical adsorption density was investigated when the reaction time was kept at 4 h, as shown in FIG. 16. For MI-(f)GDPGYIGSR, both peptide surface density and peptide adsorption density (for control) increased linearly with increasing peptide aqueous concentrations. For MI-GDPGYIGSR, peptide surface density increased with increasing MI-GDPGYIGSR concentrations (≤0.32 mM). The amount of physically absorbed GDPGYIGSR on all surfaces is little, less than 2 pmol/cm$^2$.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A composition comprising:
   a nanoparticle or microparticle comprising a biodegradable, amphiphilic, copolymer that self-aggregates to form a structure with a hydrophobic interior and a hydrophilic outer surface; and
   a biomolecule covalently linked to the nanoparticle or microparticle;
   wherein the covalent link between the biomolecule and the nanoparticle or microparticle comprises a ring formed by a Diels Alder cycloaddition or a Huisgen 1,3-dipolar cycloaddition reaction between a first unsaturated functional group attached to the polymer and a second, complementary, unsaturated functional group attached to the biomolecule.

2. The composition of claim 1 wherein said first and second unsaturated functional groups which react with each other by said Diels-Alder cycloaddition include a diene and a dienophile, and wherein said first and second unsaturated functional groups which react with each other by said Huisgen 1,3-dipolar cycloaddition include an alkyne group and an azide group.

3. The composition according to claim 2 wherein said diene is selected from the group consisting of furan and derivatives thereof, cyclopentadiene and derivatives thereof, butadiene and derivatives thereof, and cyclohexadiene and derivatives thereof, and wherein said dienophile is selected from the group consisting of maleimide and derivatives thereof, acrylonitrile and derivatives thereof, acrylamide and derivatives thereof, methyl vinyl ketone and derivatives thereof, esters of maleic acid and derivatives thereof, esters of fumaric acid and derivatives thereof, esters of acrylic acid and derivatives thereof, maleic anhydride and derivatives thereof, esters and amides of but-2-ynedioic acid and derivatives thereof, quinone and derivatives thereof, and substituted acetylenes and derivatives thereof.

4. The composition according to claim 2 wherein said diene is furan and said dienophile is maleimide.

5. The composition according to claim 2 wherein said alkyne group is selected from the group consisting of terminal alkynes and alkynes substituted with alkyl groups and derivatives thereof, ester groups and derivatives thereof, amide groups and derivatives thereof, alkyl and polyoxoalkyl groups and derivatives thereof, aryl groups and derivatives thereof, phenyl groups and derivatives thereof, and benzyl groups and derivatives thereof, and wherein said azide group is selected from the group consisting of alkyl and polyoxoalkyl azides and derivatives thereof, aryl azides and derivatives thereof, and benzyl azides and derivatives thereof.

6. The composition according to claim 5 wherein said alkyne group is an amide of propargylamine, and said azide is a substituted benzyl azide.

7. The composition of claim 1, wherein the biodegradable, amphiphilic, copolymer is selected from the group consisting of block copolymers, terpolymers, graft copolymers, and graft terpolymers.

8. The composition of claim 1 wherein the biodegradable, amphiphilic, copolymer is selected from the group consisting of polymers of natural origin, polymers produced by chemical synthesis and polymers produced by biological synthesis, and wherein said polymers of natural origin are selected from the group consisting of proteins, polysialic acids, hyaluronic acid and derivatives thereof, polysaccharides and derivatives thereof, chitosan and derivatives thereof, alginate and derivatives thereof, collagen and derivatives thereof, and aliphatic poly(esters), polycarbonates and derivatives thereof, poly (hydroxyalkanoates) and derivatives thereof, and wherein said polymers produced by biological synthesis include polymers synthesized by fermentation, and wherein said polymers produced by chemical synthesis include polymers produced by ring-open polymerization, polycondensation, free radical polymerization, or ionic polymerization.

9. The composition of claim 1 wherein said biodegradable copolymer is selected from the group consisting of polyesters, polycarbonates, polyamides, poly(esteramide)s, poly (anhydride)s, polyurethanes, poly(ester-urethane)s, poly(hydroxyalkanoate)s, and combinations thereof.

10. The composition according to claim 1 wherein said microparticle or nanoparticle comprises one or more therapeutic agents encapsulated in said interior of said polymer microparticle or polymer nanoparticle.

11. The composition according to claim 1 wherein said biomolecule is covalently bound to said outer surface of said microparticle or nanoparticle.

12. The composition according to claim 1 wherein said Huisgen 1,3-dipolar cycloaddition is Cu(1) catalyzed.

13. The composition according to claim 1, wherein the nanoparticle or polymer microparticle is a nanosphere.

14. The composition according to claim 1, wherein the nanoparticle or polymer microparticle is a microsphere.

15. The composition according to claim 1, wherein the biodegradable, amphiphilic, copolymer is a poly(trimethylene carbonate)-based copolymer.

16. The composition according to claim 1, wherein the biodegradable, amphiphilic, copolymer is a poly(lactide)-based copolymer.

17. The composition according to claim 16, wherein the biodegradable, amphiphilic, copolymer comprises a poly (ethylene glycol) segment.

18. The composition according to claim 1, wherein the copolymer is an aliphatic polyester copolymer.

19. The composition according to claim 1, wherein the copolymer is a polycarbonate copolymer.

20. The composition according to claim 1, wherein the copolymer is a block copolymer or a graft copolymer.

21. The composition according to claim 1, wherein the copolymer comprises hydrophilic and hydrophobic domains.

22. The composition according to claim 1, wherein the copolymer is a terpolymer.

23. The composition according to claim 1, wherein the nanoparticle or microparticle is a nanoparticle.

24. The composition according to claim 23, wherein the nanoparticle or microparticle is a nanoparticle with a size of about 200 nm or less.

25. The composition according to claim 1, wherein the nanoparticle or microparticle is a microparticle.

26. The composition according to claim 1, wherein the biomolecule is a therapeutic biomolecule.

27. The composition according to claim 1, wherein the biomolecule is a peptide, polypeptide or protein.

28. The composition according to claim 1, wherein the biomolecule is a nucleic acid.

29. The composition according to claim 1, wherein the biomolecule is an antibody or fragment thereof.

30. A composition comprising:
  a nanoparticle or microparticle-comprising a polymer wherein said polymer is a poly(2-methyl-2-carboxytrimethylene carbonate-co-lactide)-graft-poly(ethylene glycol) polymer or a poly(2-allyloxymethyl-2-methyl-trimethylene carbonate-co-lactide) polymer;
  a biomolecule covalently linked to the nanoparticle or microparticle;
  wherein the covalent link between the biomolecule and the nanoparticle or microparticle comprises a ring formed by a Diels Alder cycloaddition or a Huisgen 1,3-dipolar cycloaddition reaction between a first unsaturated functional group attached to the polymer and a second, complementary, unsaturated functional group attached to the biomolecule.

31. The composition according to claim 30, wherein said polymer is a poly(2-methyl-2-carboxytrimethylene carbonate-co-lactide)-graft-poly(ethylene glycol) polymer.

32. The composition according to claim 31, wherein first unsaturated functional group attached to the polymer comprises a furan ring, a terminal alkyne group, or an azide group.

33. The composition according to claim 30, wherein said polymer is a poly(2-allyloxymethyl-2-methyl-trimethylene carbonate-co-lactide) polymer.

34. The composition according to claim 33, wherein the first unsaturated functional group attached to the polymer comprises a furan ring.

35. A method of delivering a biomolecule into a biological system comprising introducing a composition according to claim 1 into the biological system.

36. A method of delivering a biomolecule to an animal comprising administering to the animal a composition according to claim 1.

37. A method of delivering a biomolecule to a human comprising administering to the human a composition according to claim 1.

\* \* \* \* \*